US006829496B2

(12) United States Patent
Nagai et al.

(10) Patent No.: US 6,829,496 B2
(45) Date of Patent: Dec. 7, 2004

(54) BLOOD COMPONENT MEASUREMENT APPARATUS

(75) Inventors: Yoshiroh Nagai, Nishinomiya (JP); Shinji Yamamoto, Sakai (JP); Akihiro Ukai, Toyokawa (JP)

(73) Assignee: Minolta Co., Ltd., Osaka (JP)

( * ) Notice: Subject to any disclaimer, the term of this patent is extended or adjusted under 35 U.S.C. 154(b) by 0 days.

(21) Appl. No.: 10/298,949

(22) Filed: Nov. 19, 2002

(65) Prior Publication Data

US 2003/0114737 A1 Jun. 19, 2003

(30) Foreign Application Priority Data

Nov. 20, 2001 (JP) .................................... 2001-354944

(51) Int. Cl.$^7$ ............................................... A61B 5/00
(52) U.S. Cl. ................................... 600/322; 600/336
(58) Field of Search ................................ 600/310, 322, 600/323, 330, 336

(56) References Cited

U.S. PATENT DOCUMENTS

| 4,653,498 A | | 3/1987 | New et al. |
| 4,781,195 A | * | 11/1988 | Martin .................... 600/336 |
| 4,846,183 A | * | 7/1989 | Martin .................... 600/336 |
| 5,193,543 A | | 3/1993 | Yelderman |
| 5,348,005 A | * | 9/1994 | Merrick et al. ........... 600/330 |
| 5,766,127 A | * | 6/1998 | Pologe et al. ............ 600/310 |
| 5,800,348 A | * | 9/1998 | Kaestle .................... 600/322 |
| 5,954,644 A | | 9/1999 | Dettling et al. |

* cited by examiner

Primary Examiner—Eric F. Winakur
(74) Attorney, Agent, or Firm—McDermott Will & Emery LLP

(57) ABSTRACT

In a pulse oximeter (blood component measurement apparatus), a subject body is irradiated periodically with red light and infrared light. Then, carried out sequentially in a time sharing manner are the measurement of the transmitted light intensity through the subject body, the measurement of the pulse wave component of the transmitted light intensity, and the measurement of the dark level in the state that the subject body is not irradiated with the light. On the basis of these measurement values, oxygen saturation of the arterial blood is measured. In the present embodiments, each measurement is carried out with a time interval equal to the period corresponding to the line frequency. In this approach, periodic noise of the line frequency or other noise are eliminated in dark level correction. This permits precise measurement of the blood component.

14 Claims, 18 Drawing Sheets

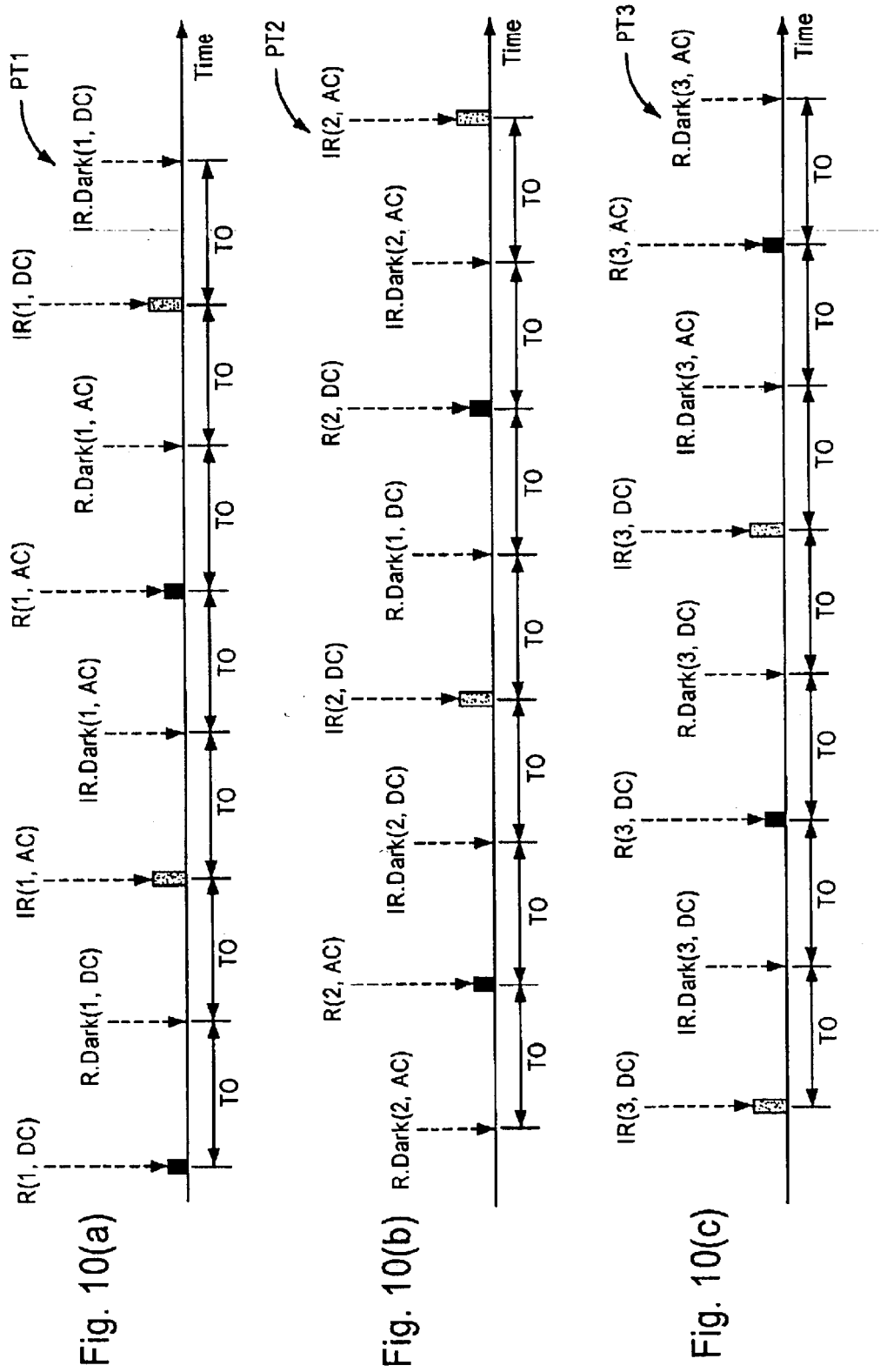

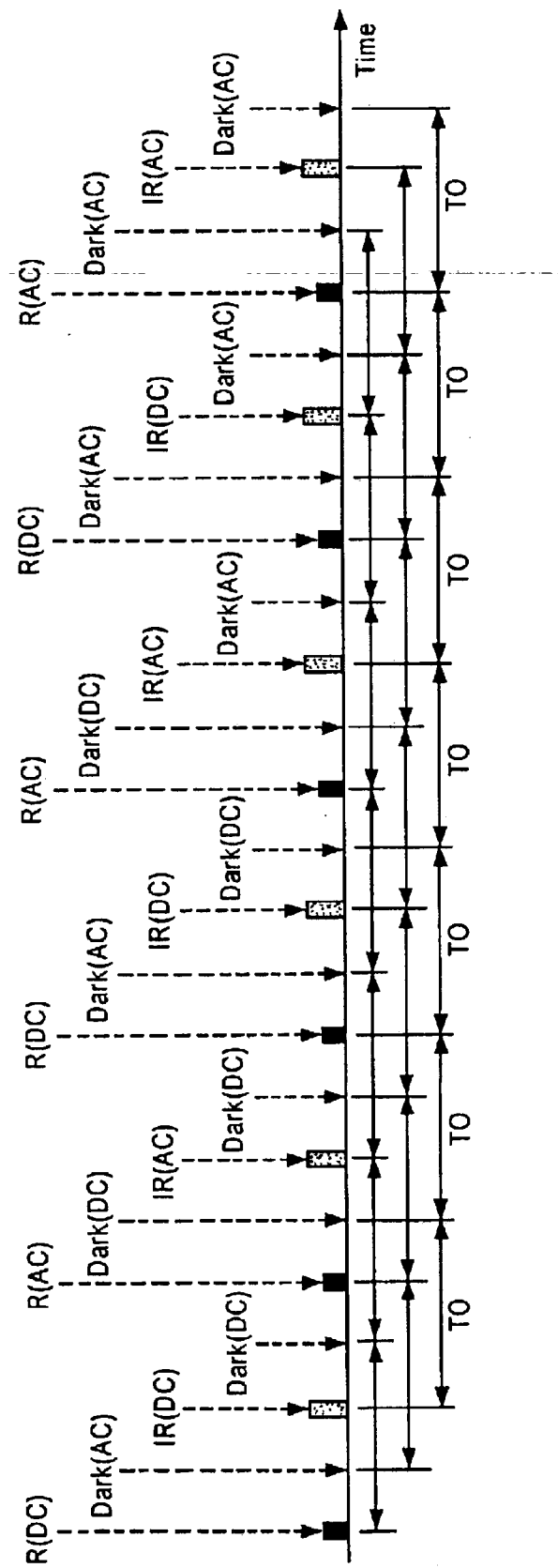

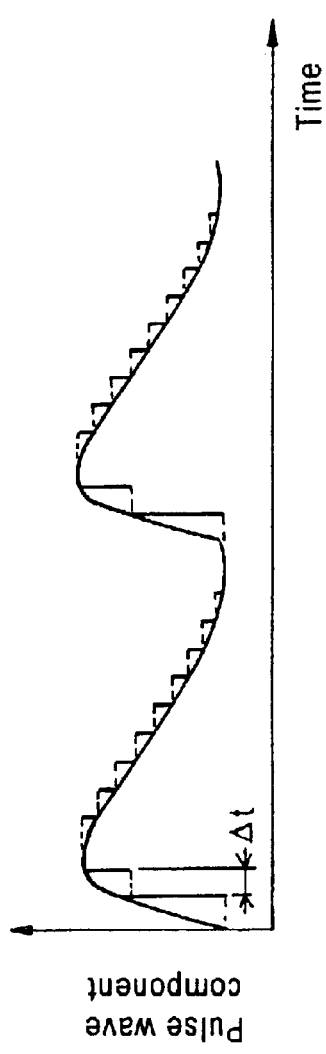
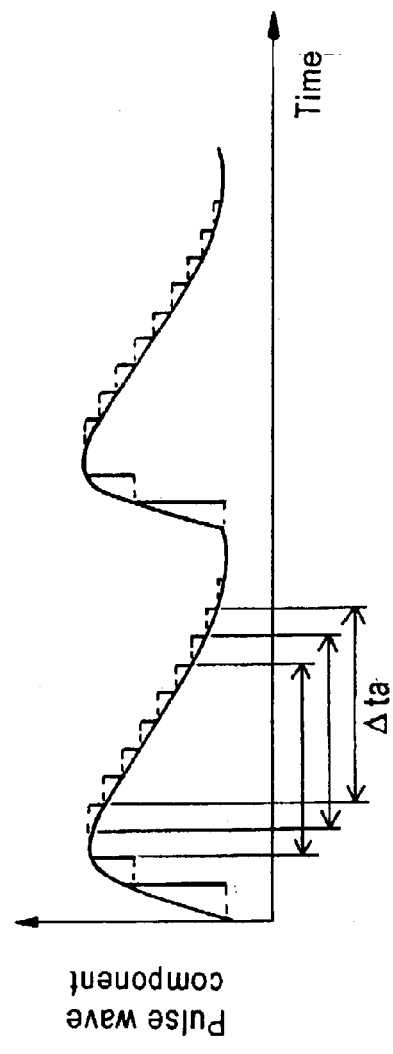
Fig. 18(a)
Fig. 18(b)

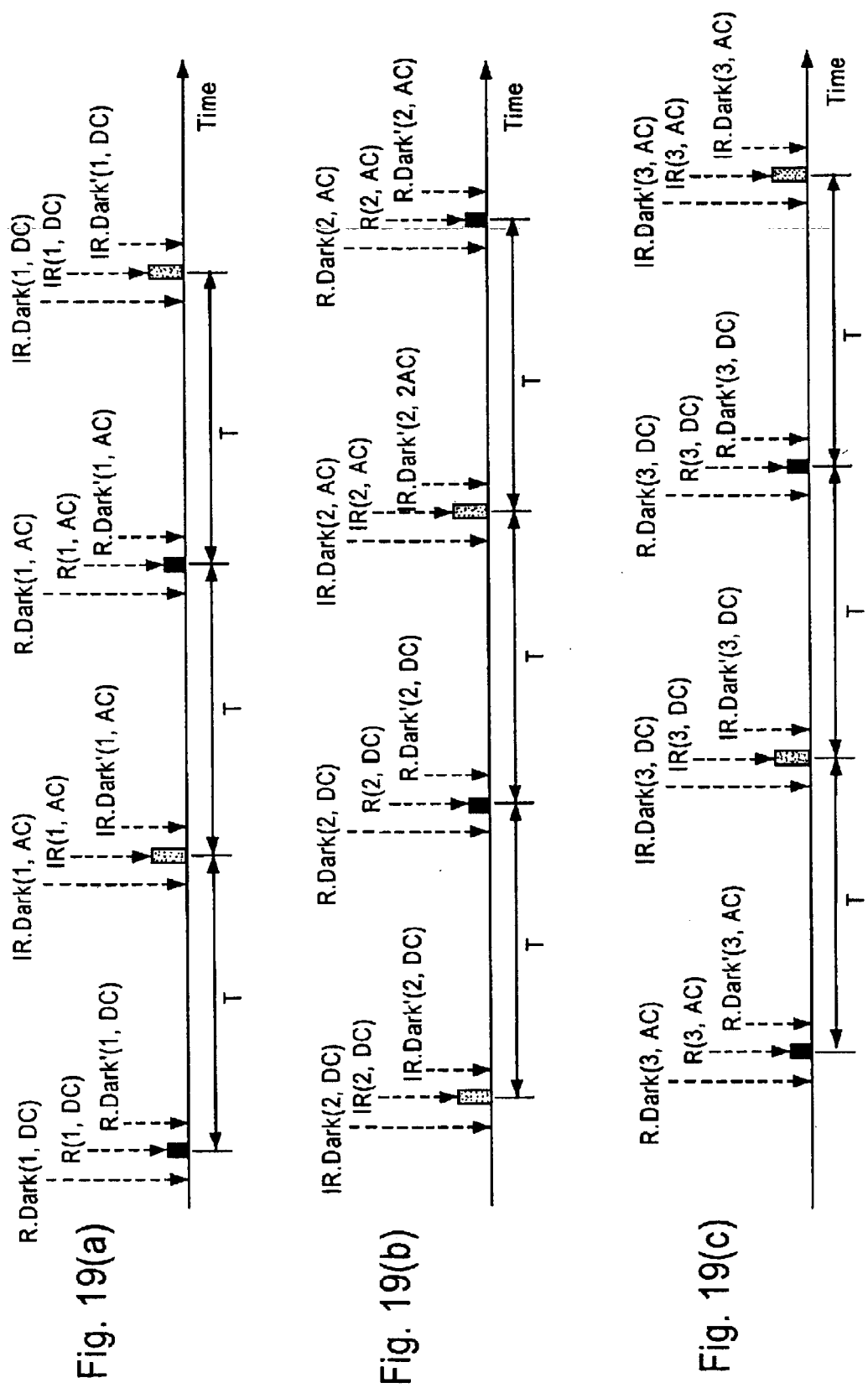

BLOOD COMPONENT MEASUREMENT APPARATUS

This application is based on the application No. 2001-354944 filed in Japan, the content of which is hereby incorporated by reference.

BACKGROUND OF THE INVENTION

1. Field of the Invention

The present invention relates to a blood component measurement apparatus such as a pulse oximeter.

2. Related Art of the Invention

In a blood component measurement apparatus such as a pulse oximeter, a light emitting element emits light. The light transmitted through a subject body (the body of a subject person) is then measured by an electric circuit comprising a photodetector, whereby oxygen saturation or the like of the blood is obtained.

Nevertheless, in such a blood component measurement apparatus, the measurement signal can contain periodic noise, such as induced noise of line frequency and that due to light from fluorescent lamps. Thus, since the level of the measurement signal of the transmitted light detected by the photodetector is very low, the influence of such periodic noise needs to be eliminated in order that the blood component is measured precisely.

The invention has been devised to resolve this problem. The object of the invention is to provide a blood component measurement apparatus for measuring a blood component precisely.

SUMMARY OF THE INVENTION

In order to resolve the above-mentioned problem, a blood component measurement apparatus for measuring a blood component in the arterial blood of a subject body according to the invention comprises: an illuminating device for illuminating said subject body with predetermined light periodically at first timings; a light intensity detector for detecting light intensity measurement values of light transmitted through said subject body; a dark level detector for detecting dark level measurement values periodically at second timings without illumination from said illuminating device; a pulse wave detector for extracting pulse wave component from said light intensity measurement values, and thereby detecting pulse wave measurement values; and a blood component measurer for measuring the blood component of said arterial blood on the basis of said light intensity measurement values, said dark level measurement values, and said pulse wave measurement values; wherein each time interval between said first timings and said second timings corresponds to a line frequency.

In the following description, like parts are designated by like reference numbers throughout the several drawings.

BRIEF DESCRIPTION OF THE DRAWINGS

FIG. 10 illustrates the operation of a pulse oximeter 1C according to Embodiment 3 of the invention;

FIG. 11 illustrates the timing of measurement in a pulse oximeter 1C;

FIG. 18 illustrates time difference values of a pulse wave component in a pulse oximeter 1F;

FIG. 19 illustrates the timing of measurement according to a modification of the invention.

DETAILED DESCRIPTION OF THE PREFERRED EMBODIMENTS

Embodiment 1

Principles of Measurement in Pulse Oximeter

A pulse oximeter 1A (FIG. 1) according to Embodiment 1 of the invention measures a blood component in the arterial blood of a subject body or, specifically, the oxygen saturation of the blood. Described below are the principles of the measurement of oxygen saturation in the pulse oximeter 1A.

Figure 2:
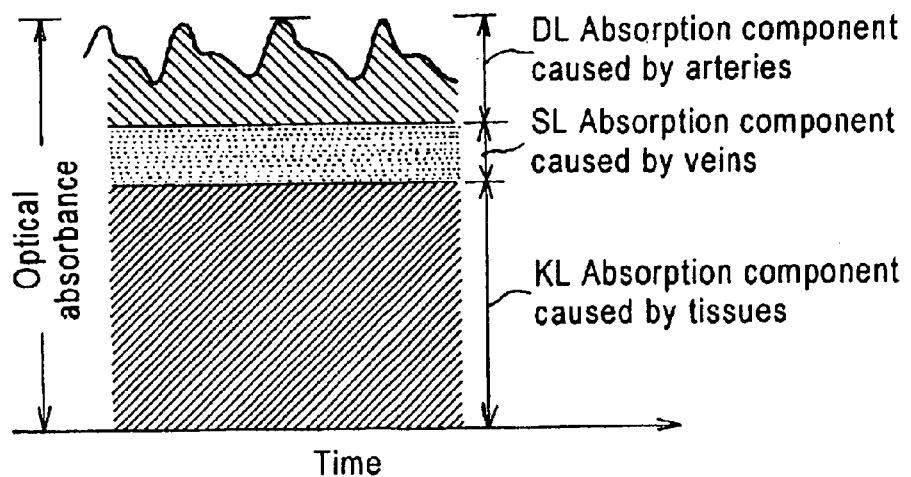
FIG. 2 illustrates optical absorbance in a subject body.

FIG. 2 illustrates optical absorbance in a subject body. In FIG. 2, the horizontal axis indicates time, while the vertical axis indicates optical absorbance.

When a subject body is irradiated with light, a part of the light is absorbed. The light absorption is divided into an absorption component KL caused by tissues, an absorption component SL caused by veins, and an absorption component DL caused by arteries. In the absorption component DL caused by arteries, the optical absorbance varies in the same rate as the pulse.

Figure 3:
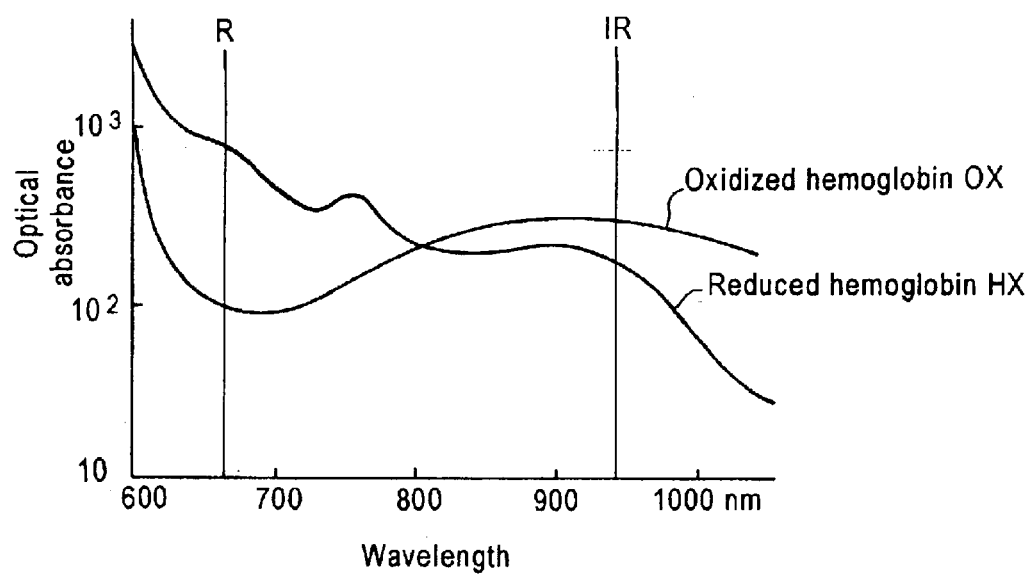
FIG. 3 shows absorption spectra of oxidized hemoglobin and reduced hemoglobin.

FIG. 3 shows absorption spectra of oxidized hemoglobin and reduced hemoglobin. In FIG. 3, the horizontal axis indicates the wavelength of light, while the vertical axis indicates optical absorbance. The absorbance spectrum OX of oxidized hemoglobin and the absorbance spectrum HI of reduced hemoglobin have different shapes from each other. At a wavelength of red light R, reduced hemoglobin has the higher absorbance. In contrast, at a wavelength of infrared light IR, oxidized hemoglobin has the higher absorbance.

As a result of this difference in the absorbance spectra OX and HI, a higher oxygen saturation of the blood causes a higher absorbance in the infrared light IR, while lower oxygen saturation of the blood causes a higher absorbance in the red light R. Using this phenomenon, the pulse oximeter 1A measures the oxygen saturation of the blood on the basis of the ratio between the pulse wave components Ma(R) and Ma(IR) (see FIG. 6) in the transmitted red light R and the transmitted infrared light IR after the transmission through the subject body.

In the measurement of the ratio between the pulse wave component amplitudes of the transmitted red light and the transmitted infrared light, it is taken into account that the intensity of each transmitted light is proportional to the intensity of the emitted light from the light source. That is, each pulse wave component amplitude is divided by the transmitted light intensity, whereby avoided is the influence of the intensity of the emitted light from the light source.

Figure 4A:
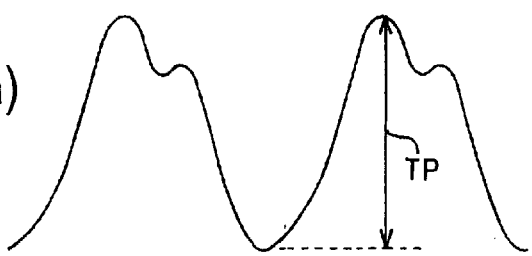
FIG. 4 illustrates time difference values of a pulse wave component.
Figure 4B:
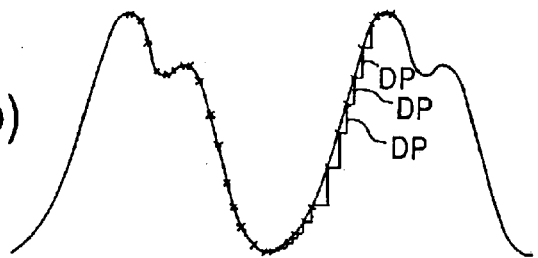

Further, in the measurement of the ratio between the pulse wave component amplitudes of the transmitted red light and the transmitted infrared light, not used is the difference TP between the peek and the valley of a pulse as shown in FIG. 4(a). Instead, a pulse is divided into finite time intervals as shown in FIG. 4(b), whereby the difference values (time difference values, hereafter) DP's in these intervals are used. This approach increases the number of samples.

The ratio between the time difference value of the pulse wave component and the transmitted light intensity is calculated for each of the red light and the infrared light. Then, a p-value is calculated from these ratios according to the following Formula (1).

$$p = \frac{\frac{R(t + \Delta t) - R(t)}{R(t)}}{\frac{IR(t + \Delta t) - IR(t)}{IR(t)}} \quad (1)$$

In Formula (1), R indicates the transmitted light intensity of the red light, while IR indicates the transmitted light intensity of the infrared light. .t indicates a difference time interval. As such, the p-value is calculated as the ratio between the ratios of the time difference value of the pulse wave component to the transmitted light intensity for the red light and the infrared light.

Further, prepared in advance is a table providing the relation between the p-value and the oxygen saturation of the blood. Thus, referring to this table, the oxygen saturation is obtained from the p-value calculated on the basis of the transmitted light intensity for the red light and the infrared light.

Configuration and Operation of Pulse Oximeter 1A

Figure 1:
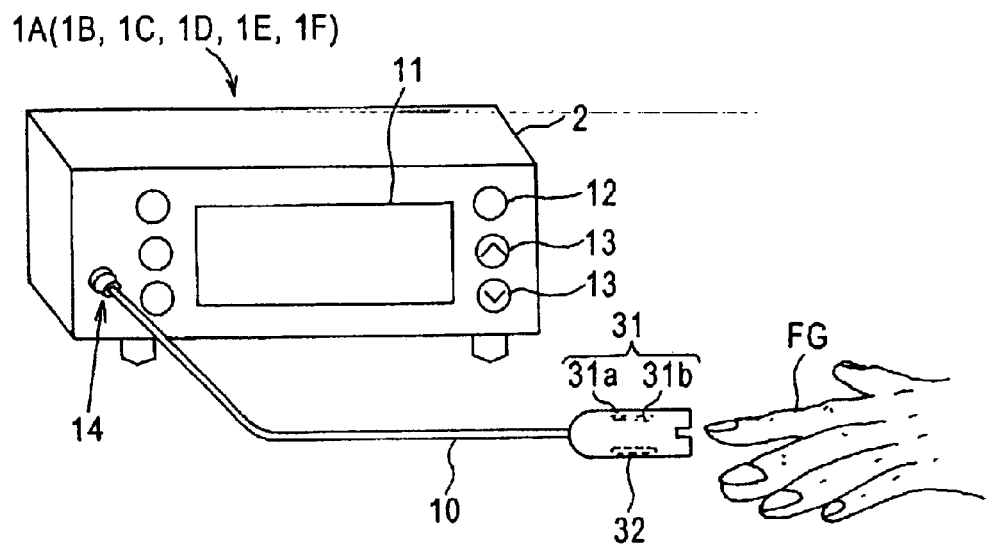
FIG. 1 shows the configuration of the main part of a pulse oximeter 1A according to Embodiment 1 of the invention.
Figure 5:
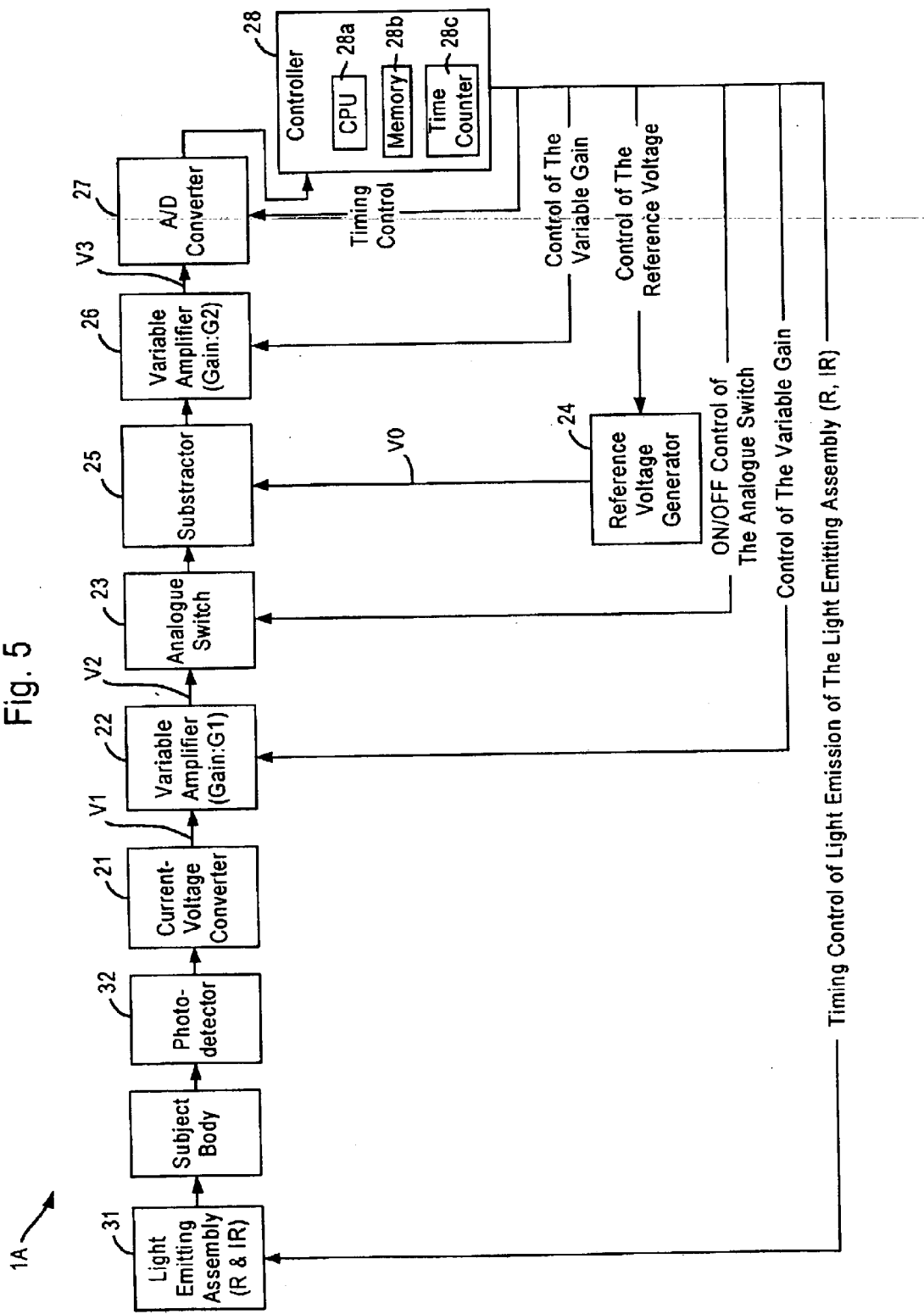
FIG. 5 shows the configuration of the measurement circuit of a pulse oximeter 1A.

FIG. 1 shows the configuration of the main part of the pulse oximeter 1A. FIG. 5 shows the configuration of the measurement circuit of the pulse oximeter 1A. The algorithm of measurement of the oxygen saturation by the pulse oximeter 1A is described below with reference to FIGS. 1 and 5.

The pulse oximeter 1A serves as a blood component measurement apparatus, and hence measures the oxygen saturation as a blood component. The pulse oximeter 1A comprises: a main body 2; and a probe 3 electrically connected to the main body 2 via a lead wire 10.

The main body 2 comprises: a display section 11 for displaying the blood component measurement result and the like; a menu button 12 for causing a menu screen to be displayed on the display section 11; two selection switches 13 used for various setting on the menu screen and the like; and a connector section 14 for connecting to an end of the lead wire 10.

The probe 3 comprises: light emitting elements 31a and 31b for emitting red light R and infrared light IR, respectively; and a photodetector 32.

In the measurement of oxygen saturation by the pulse oximeter 1A, the transmitted light intensity and the time difference value of the pulse wave component are measured for each of the red light and the infrared light as shown in Formula (1). Thus, the red and infrared light emitting elements 31a and 31b in the probe 3 emit pulsed light alternately, while the photodetector 32 measures the light transmitted through a finger FG inserted into the probe 3. The probe 3 for measuring the light intensity herein may be of a transmission type or of a reflection type. In either type, measured is the light transmitted through the arterial blood of the subject body. Accordingly, the light to be measured in either type is referred to as the transmitted light without distinction in this specification.

The output of the photodetector 32 is converted into a voltage by a current-voltage converter 21, and then amplified into an output voltage V2 by a variable amplifier 22. As for the output voltage V2, an output voltage value (dark level, hereafter) V2 (dark) in the non-light-emitted state is measured when the light emitting assembly 31 is not emitting light, while an output voltage value (transmitted light intensity measurement value, hereafter) V2(R) or V2(IR) in the light-emitted state is measured when the light emitting assembly 31 is emitting light. Then, as shown in the following Formulas (2) and (3), the difference between the dark level and the transmitted light intensity measurement value is calculated for each of the red light and the infrared light, whereby the dark level is eliminated from the transmitted light intensity measurement value (dark level correction, hereafter).

$$R(t) \propto \{V_2(R) - V_2(Dark)\}_t \quad (2)$$

$$IR(t) \propto \{V_2(IR) - V_2(Dark)\}_t \quad (3)$$

FIG. 6 shows an example of the measurement result of the transmitted light intensity V2 for the red light and the infrared light.

As shown in FIG. 6, the amplitude of the pulse wave component Ma measured in the transmitted light through the subject body is generally very small in comparison with the entirety of the transmitted light intensity. Accordingly, in order to obtain time difference values of the pulse wave component Ma by means of difference operations on the transmitted light intensity measurement value, an A/D converter 27 in the transmitted light intensity measurement needs to have a very high resolution.

Figure 6A:
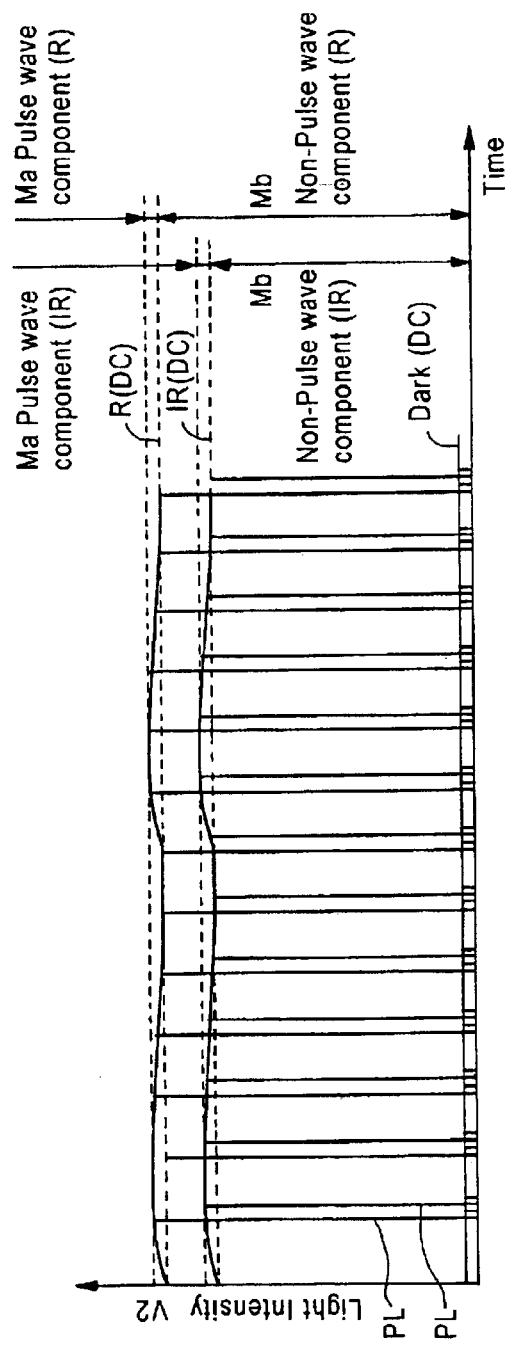
FIG. 6 shows an example of measurement result in red light and infrared light.
Figure 6B:
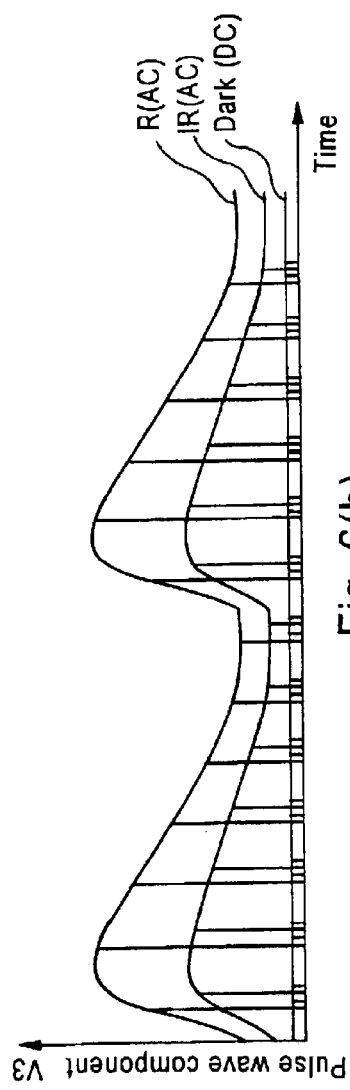

Thus, in order to avoid this necessity, in parallel to the measurement of the transmitted light intensity, the pulse wave component (pulse wave component measurement value, hereafter) in the transmitted light intensity measurement value is extracted, amplified, and A/D-converted in a predetermined electric circuit. This approach reduces quantization error and the like, and thereby permits more precise measurement of the oxygen saturation in comparison with the case that the transmitted light intensity is inputted to the A/D converter 27 and that the time difference values are then calculated. More specifically, in the measurement of the pulse wave component, a reference voltage corresponding to the non-pulse-wave component Mb is generated by a reference voltage generator 24, and then subtracted from the transmitted light intensity V2 in the subtractor 25. The output of the subtractor 25 is amplified in a variable amplifier 26, and then A/D-converted in the A/D converter 27. FIG. 6(b) shows an example of the measurement result of the pulse wave component waveform V3 outputted from the variable amplifier 26. As a result of the above-mentioned processes, the pulse wave component Ma shown in FIG. 6(a) is amplified.

Figure 7:
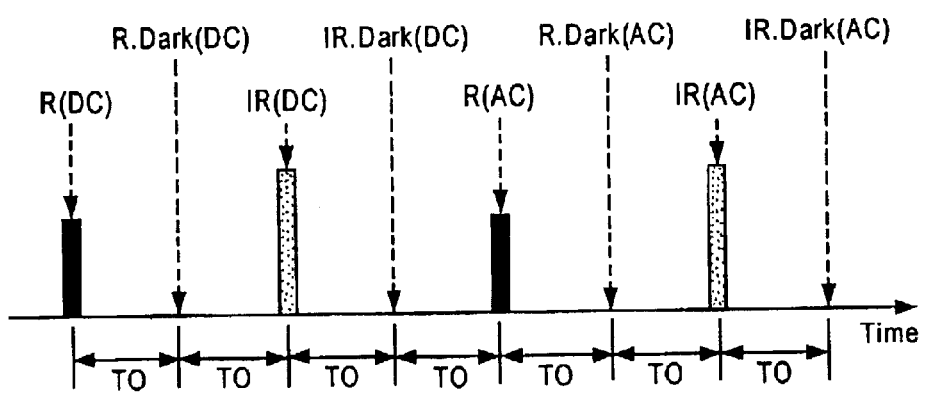
FIG. 7 illustrates the timing of measurement in a pulse oximeter 1A.

FIG. 7 illustrates the timing of measurement in the pulse oximeter 1A. In FIG. 7, R indicates a measurement with red light, while IR indicates a measurement with infrared light. DC indicates transmitted light intensity, while AC indicates pulse wave component. Dark level measurements carried out in the non-light-emitted state of the light emitting assembly 31 are common for the red light and the infrared light. However, these measurements are distinguished and labeled as R.Dark and IR.Dark, respectively, for convenience.

As shown in FIG. 7, the pulse oximeter 1A measures transmitted light intensity DC and pulse wave component AC alternately for the red light and the infrared light in a time sharing manner. That is, each of the measurement of the transmitted light intensity and the measurement of the pulse wave component is carried out in the order R.R.Dark.IR-.IR.Dark.

The measured signal can contain induced noise of line frequency and noise due to light from luminescent lamps, in addition to the signal component of the light which has been emitted from the light emitting assembly 31 and then transmitted through the subject body. In order to avoid the influence of such noise, the measurement period T0 defined as the time interval between a first timing in which an R measurement or an IR measurement is carried out and a second timing in which a dark level measurement is carried out is set equal to the period (1/50 sec or 1/60 sec) corresponding to the line frequency (50 Hz or 60 Hz). As a result, the level of periodic noise at the R and IR measurements equals that at the R.Dark and IR.Dark measurements. Accordingly, in the dark level correction in which a dark level signal is subtracted from a measured R or IR signal according to the above-mentioned Formulas (2) or (3), the periodic noise having a frequency equal to the line frequency or an integer multiple thereof is canceled. This permits precise measurement of the oxygen saturation. This situation holds true also in the dark level correction for the pulse wave component described later.

In the dark level correction, constant offset components such as the offset voltages of the amplifiers can also be eliminated.

Referring to FIG. 5 again, each circuit of the pulse oximeter 1A is described below in detail.

The light emitting assembly 31 comprises the red light emitting element 31a and the infrared light emitting element 31b. In order to measure transmitted light intensity through a subject body in a time sharing manner, the light emitting assembly 31 emits pulsed red light and pulsed infrared light alternately (PL's in FIG. 6(a)).

The light emitted from the light emitting assembly 31 and then transmitted through the subject body is detected by the photodetector 32, and thereby converted into a voltage V1 proportional to the photocurrent by the current-voltage converter 21. The detection voltage V1 from the current-voltage converter 21 is amplified into an appropriate voltage level by the variable amplifier 22.

Described below are the measurement of the transmitted light intensity and the measurement of the pulse wave light intensity.

In the measurement of the transmitted light intensity, the output voltage of the reference voltage generator 24 is set at a predetermined voltage. Further, the gain of the variable amplifier 22 is set at a predetermined gain, whereby the transmitted light intensity voltage V2 is measured. In this measurement of the transmitted light intensity, the above-mentioned setting values are not changed.

In response to a transmitted light intensity signal outputted from the A/D converter 27, a controller 28 adjusts the gain G2 of the variable amplifier 26 such that the output from the variable amplifier 26 is maintained within the available output voltage range thereof. The controller 28 further adjusts the emitted light intensities of the light emitting elements 31a and 31b such that the measurement values of the transmitted light intensities of the red light and the infrared light are close to each other (substantially the same value).

In the measurement of the pulse wave component, a DC voltage V0 corresponding to the non-pulse-wave component Mb (see FIG. 6(a)) is generated for each of the R, IR, and Dark measurements, by the reference voltage generator 24. The voltage V0 corresponding to the non-pulse-wave component is subtracted from the output voltage V2 corresponding to the transmitted light intensity in the subtractor 25. The reference voltage generator 24 may be composed of a D/A converter. Then, the variable amplifier 26 outputs a pulse wave component waveform as shown in FIG. 6(b). This pulse wave component voltage is converted into a digital signal by the A/D converter 27.

In response to the pulse wave amplitude waveform (the value of pulse wave component Ma shown in FIG. 6(a)) obtained in the measurement of the transmitted light intensity, the gain G2 of the variable amplifier 26 is adjusted such that the amplitude of the amplified pulse wave voltage V3 is maintained within the measurable range of the A/D converter 27.

The voltage setting value for the reference voltage generator 24 in the measurement of the pulse wave component is determined on the basis of: the pulse wave component information (the value of Ma) obtained by the measurement of the transmitted light intensity; the non-pulse-wave component information (the value of non-pulse-wave component Mb shown in FIG. 6(a)); and the gain G2 which is set in the variable amplifier 26. Accordingly, the reference voltage value is set such that the pulse wave waveform voltage V3 from which the reference voltage has been subtracted and which has been amplified is maintained within the measurable range of the A/D converter 27.

The setting value for the voltage of the reference voltage generator 24 and the setting value for the gain G2 of the variable amplifier 26 are determined on the basis of the measurement result of the transmitted light intensity. Renewal of these setting values are determined on the basis of the measurement data of the transmitted light intensity measurement value through the subject body obtained in a measurement of the transmitted light intensity for a predetermined time duration (for example, past 3 sec) immediately before the renewal. Preferably, this predetermined time duration is a measurement time duration covering at least one period of the pulse wave data, that is, a time duration sufficient to obtain the amplitude information of the pulse wave component.

The reference voltage of the reference voltage generator 24, the gain G1 of the variable amplifier 22, the gain G2 of the variable amplifier 26, and the intensity (the value of the driving current) of the light emitting assembly 31 are renewed in every predetermined time interval (for example, every 1 second).

Similarly to the measurement of transmitted light intensity, in the measurement of the pulse wave component, dark level correction is carried out in order to eliminate the dark level. That is, operations are applied according to the right side of the following formulas (4) and (5).

$$R(t+\Delta t)-R(t) \propto \{V_3(R)-V_3(Dark)\}_{t+\Delta t} - \{V_3(R)-V_3(Dark)\}_t \quad (4)$$

$$IR(t+\Delta t)-IR(t) \propto \{V_3(IR)-V_3(Dark)\}_{t+\Delta t} - \{V_3(IR)-V_3(Dark)\}_t \quad (5)$$

An analogue switch 23 is used for the calibration of the A/D converter 27 by means of the reference voltage from the reference voltage generator 24. The output of the variable amplifier 22 is shut off before a measurement, whereby the A/D converter 27 is adjusted such that the measurement value from the A/D converter 27 equals the reference voltage value.

The measurement data obtained in the above-mentioned measurement circuit is provided to the controller 28, whereby the p-value is calculated according to the following Formula (6).

$$p = \frac{\frac{\{V_3(R) - V_3(Dark)\}_{t+\Delta t} - \{V_3(R) - V_3(Dark)\}_t}{\{V_2(R) - V_2(Dark)\}_t}}{\frac{\{V_3(IR) - V_3(Dark)\}_{t+\Delta t} - \{V_3(IR) - V_3(Dark)\}_t}{\{V_2(IR) - V_2(Dark)\}_t}} \quad (6)$$

The controller 28 comprises: a CPU 28a; and a memory 28b composed of a ROM or the like. The controller 28 is a digital circuit for controlling the above-mentioned circuit sections comprehensively. The controller 28 further comprises a timer counter 28c for managing the timing of measurement and the timing of light emission of the light emitting assembly.

The controller 28 may apply digital filtering such as low-pass filtering and high-pass filtering, onto the measurement data.

In the calculation of time difference values of the pulse wave component, when the setting values for the reference voltage of the reference voltage generator 24 at measurement timings t and t+.t are different from each other, the above-mentioned p-value (or equivalently, the oxygen saturation of the blood) is not calculated using these measurement values. This is because in such a case, when a difference between the output voltage values of the reference voltage generator 24 is calculated from a difference between the reference voltage setting values, there is a discrepancy between the setting value for the reference voltage of the reference voltage generator 24 and the actual output voltage. This results in an insufficient precision.

In the measurement of the transmitted light intensity and the measurement of the dark level thereof, the gain G1 of the variable amplifier 22 is set equal to the gain G2 of the variable amplifier 26. Otherwise, precise dark level correction is not achieved. In the measurement of the pulse wave component and the measurement of the dark level thereof, the gain G1 of the variable amplifier 22 is set equal to the gain G2 of the variable amplifier 26.

In the measurement of transmitted light intensity and the measurement of the pulse wave component, measurement operations are carried out alternately for the red light R and the infrared light IR. Accordingly, the time points of measurement are different for the measurement data of R and IR. Thus, simulated measurement values for R and IR at the same time point are calculated by interpolation of the measurement data before and after the time point of data measurement.

Then, referring to the table which is stored in the memory 28a and which provides the relation between the p-value and the oxygen saturation of the blood, the controller 28 obtains the oxygen saturation of the blood from the p-value calculated according to Formula (6). The obtained oxygen saturation is displayed on the display section 11.

In the above-mentioned operation of the pulse oximeter 1A, the period of the timing of measurement is set equal to an integer multiple of the period corresponding to the line frequency, whereby periodic noise of line frequency is eliminated. This permits precise measurement of oxygen saturation.

Embodiment 2

The configuration of a pulse oximeter 1B according to Embodiment 2 of the invention is similar to that of the pulse oximeter 1A according to Embodiment 1. However, in contrast to the pulse oximeter 1A, the pulse oximeter 1B comprises two A/D converters.

Figure 8:
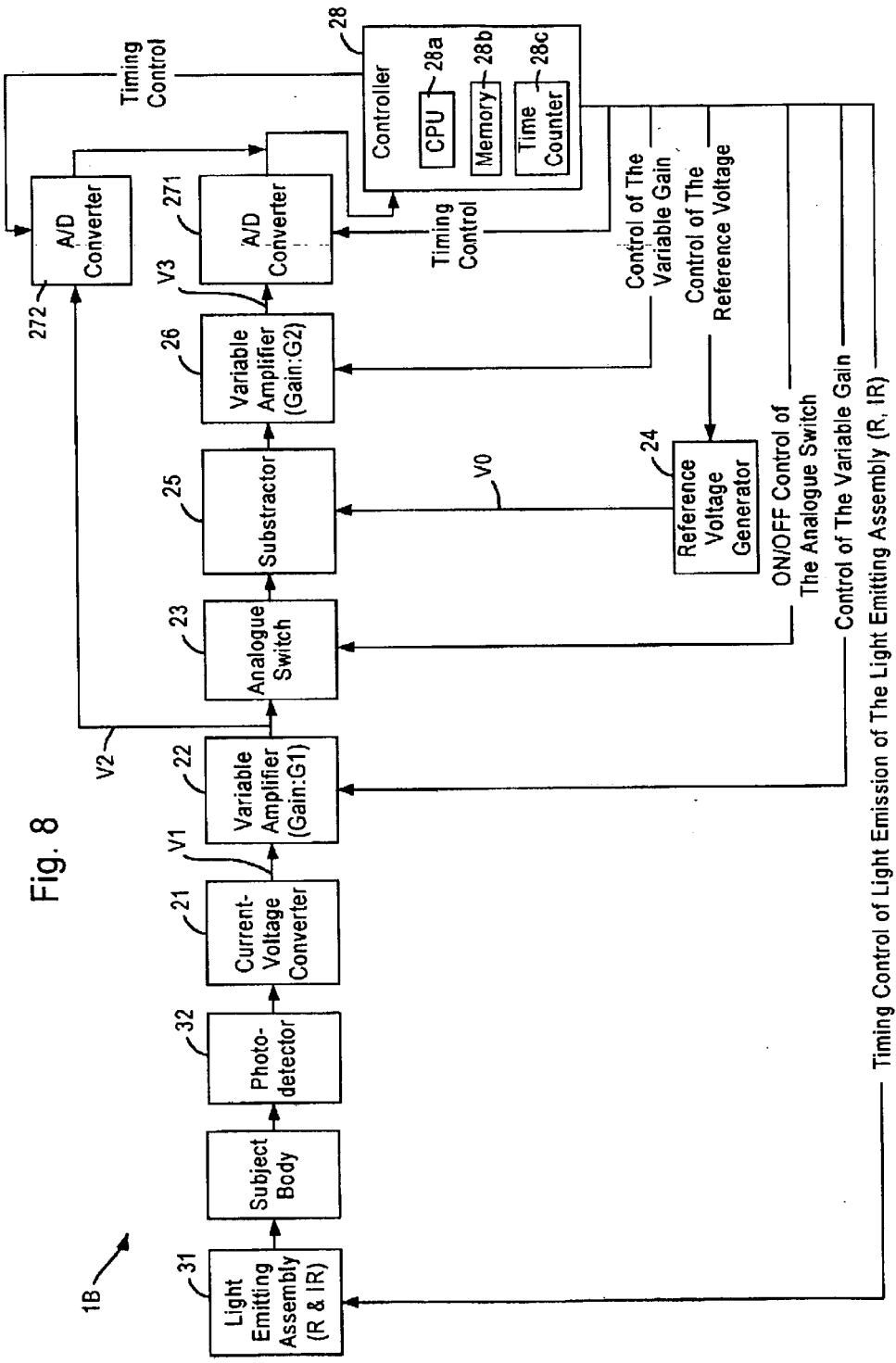
FIG. 8 shows the configuration of the measurement circuit of a pulse oximeter 1B according to Embodiment 2 of the invention.

FIG. 8 shows the configuration of the measurement circuit of the pulse oximeter 1B.

In contrast to the pulse oximeter 1A (FIG. 5), the pulse oximeter 1B comprises an A/D converter 272 in addition to an A/D converter 271.

Figure 9A:
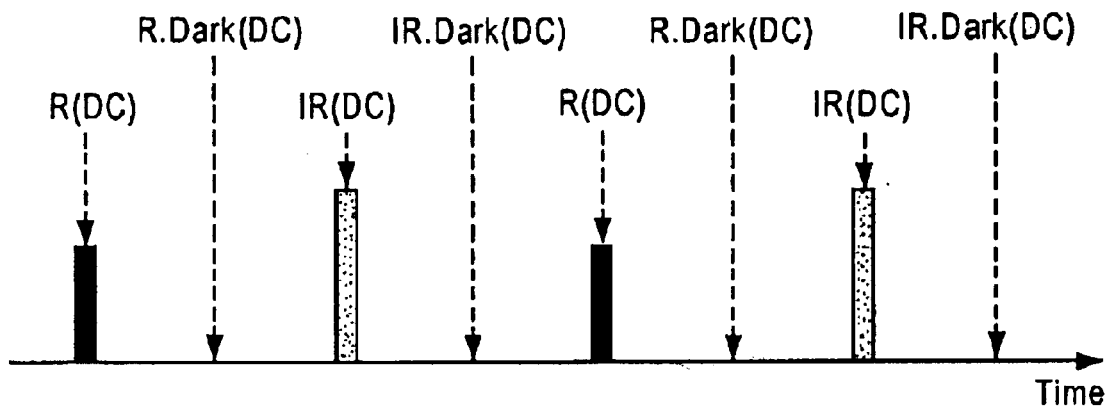
FIG. 9 illustrates the timing of measurement in a pulse oximeter 1B.
Figure 9B:
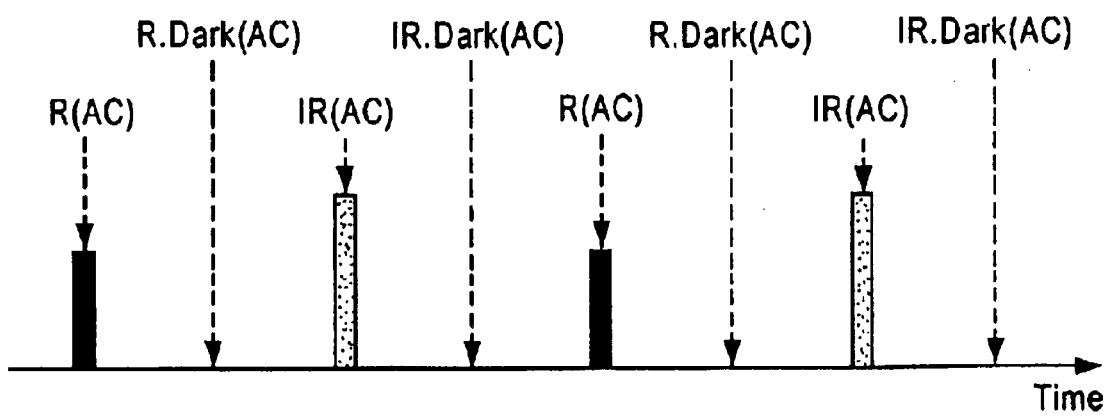

This configuration of the pulse oximeter 1B permits the measurement of R, R.Dark, IR, and IR.Dark in the timing of measurement shown in FIG. 9. In FIGS. 9(a) and 9(b), the horizontal axis indicates the time. FIG. 9(a) illustrates the timing of measurement of the transmitted light intensity. FIG. 9(b) illustrates the timing of measurement of the pulse wave component.

In the pulse oximeter 1A according to Embodiment 1, the measurement of the transmitted light intensity DC and the measurement of the pulse wave component AC have been carried out alternately. In contrast, in the pulse oximeter 1B, the measurement of the transmitted light intensity DC and the measurement of the pulse wave component AC are carried out simultaneously using the two A/D converters 271 and 272. Also in this case, the interval between the measurements of R, R.Dark, IR, and IR.Dark is set equal to the period corresponding to the line frequency. This approach provides twice the number of measurement data points in a unit time in comparison with the case of the pulse oximeter 1A.

Similarly to Embodiment 1, in the above-mentioned operation of the pulse oximeter 1B, periodic noise of line frequency is eliminated. This permits precise measurement of oxygen saturation. Further, since the transmitted light intensity and the pulse wave component are measured simultaneously, twice the number of measurement data points are obtained. This improves further the precision in the measurement of oxygen saturation.

Embodiment 3

The configuration of a pulse oximeter 1C according to Embodiment 3 of the invention is similar to that of the pulse oximeter 1A according to Embodiment 1. However, these pulse oximeters are different from each other in the configuration of the controller 28.

In general, a larger number of measurement data points permits more precise measurement of oxygen saturation of the blood. According to the configuration of the pulse oximeter 1C, three times the number of measurement data points are obtained in comparison with the case of the pulse oximeter 1A.

In the controller 28 of the pulse oximeter 1C, a memory 28b stores a program for causing the pulse oximeter 1C to execute the operation described below.

As described above, in the calculation of oxygen saturation according to Formula (6), simulated measurement values for R and IR at the same time point are calculated by interpolation of the measurement data before and after the time point of data measurement. Nevertheless, when the interval between measurement operations of the measurement data before and after the time point of the interpolation becomes longer, the precision decreases in the interpolation, and hence the precision decreases in the measurement of the oxygen saturation. Thus, in the pulse oximeter 1C, with maintaining the capability of eliminating periodic noise having a frequency equal to an integer multiple of the line frequency, the precision is improved in the interpolation of the R and IR data, while an increased number of measurement data points are obtained, whereby the precision is improved in the measurement of the oxygen saturation.

FIG. 10 illustrates the operation of the pulse oximeter 1C. In the FIG., the horizontal axis indicates the time. FIGS. 10(a)-10(c) illustrate the timing of measurement of R, R.Dark, IR, and IR.Dark for the transmitted light intensity DC and the pulse wave component AC.

As shown in FIGS. 10(a)-10(c), in the pulse oximeter 1C, the measurement pattern shown in FIG. 7 is superposed three times with an interval of TO/3 (where TO indicates the period corresponding to the line frequency), that is, with a phase shift of 120 degrees. Each index 1–3 in the timing of measurement shown in the FIG. indicates a phase number. More specifically, measurement pattern PT1 (FIG. 10(a)) indicates a first phase. Measurement pattern PT2 (FIG. 10(b)) indicates a second phase, while measurement pattern PT3 (FIG. 10(c)) indicates a third phase. In each measurement pattern P1-P3, similarly to Embodiment 1, the time interval in the timing of the measurement of R, R.Dark, IR, and IR.Dark equals the period TO corresponding to the line frequency. Accordingly, similarly to the above-mentioned cases, periodic noise having a frequency equal to an integer multiple of the line frequency is eliminated in the dark level correction in which the measurement values for R and IR are corrected by subtracting a dark level measured at a time point apart therefrom by the period TO.

In the dark level correction in the pulse oximeter 1C, time-independent constant offset components are cancelled similarly to that in Embodiment 1.

FIG. 11 illustrates the overall timing of measurement in which the above-mentioned measurement patterns PT1-PT3 are superposed along the time axis of PT1. As seen from FIG. 11, data measurement is carried out in three times the rate in the timing (FIG. 7) of measurement according to Embodiment 1.

Similarly to Embodiment 1, in the above-mentioned operation of the pulse oximeter 1C, periodic noise of line frequency is eliminated. This permits precise measurement of oxygen saturation. Further, a plurality of measurement patterns each with a phase shift are used in combination, whereby an increased number of measurement data points are obtained. This improves further the precision in the measurement of oxygen saturation.

The present embodiment has been described for the case that the number of measurement data points is multiplied three times. However, the number may be multiplied twice, four times, or the like. In such a case that n measurement patterns are superposed, the phase shift for each measurement pattern is the value TO/n which is the time difference obtained by dividing the period corresponding to the line frequency by the number n of the measurement patterns.

Embodiment 4

The configuration of a pulse oximeter 1D according to Embodiment 4 of the invention is similar to that of the pulse oximeter 1A according to Embodiment 1. However, these pulse oximeters are different from each other in the configuration of the controller 28.

In the controller 28 of the pulse oximeter 1D, a memory 28b stores a program for causing the pulse oximeter 1D to execute the operation described below.

In the pulse oximeter 1D, oxygen saturation of the blood is measured using the pulse rate information. More specifically, S/N ratio in the calculation of time difference values is improved using the pulse rate information.

The oxygen saturation of the blood is obtained by measuring time difference values for R and IR with respect to the time interval .t, similarly to the calculation of the p-value according to Formula (6). The time difference values can be obtained from the difference of the measurement values at the adjacent measurement timings. However, in the pulse oximeter 1D, the time difference values are obtained as follows.

Figure 12A:
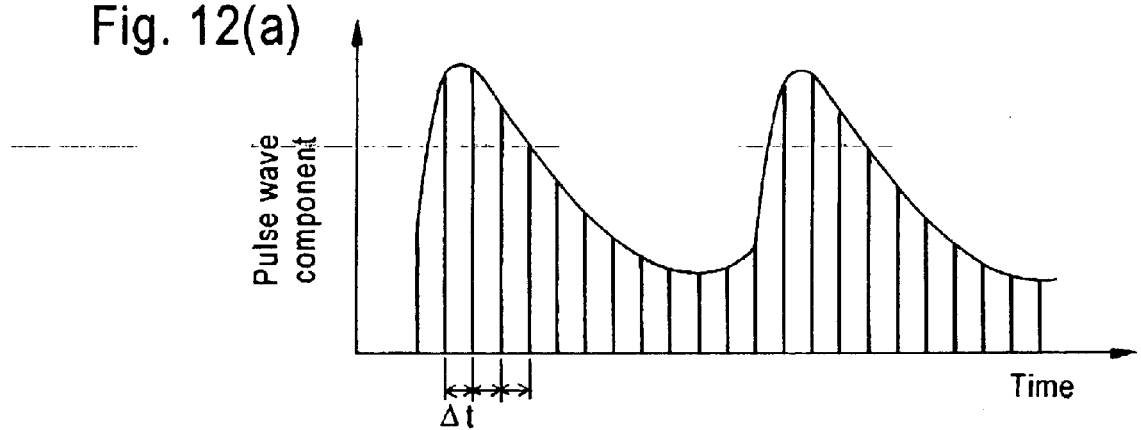
FIG. 12 illustrates the operation of a pulse oximeter 1D according to Embodiment 4 of the invention.
Figure 12B:
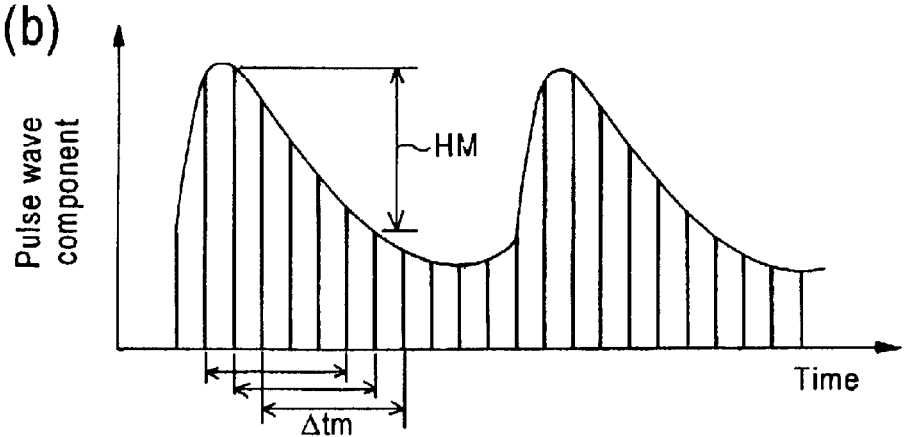

As shown in FIG. 12(b), difference between measurement values measured at two timings apart from each other by six intervals is used to calculate time difference values, whereby the p-value is calculated. As such, instead of using the measurement values at adjacent measurement timings, time difference values with a constant time interval .tm are used. That is, larger time difference values are used. This improves the S/N ratio in the calculation of the p-value and hence the oxygen saturation. Preferably, the difference time .tm shown in FIG. 12(b) is a time interval the time difference value of which corresponds substantially to the half HM of the amplitude of the pulse wave waveform (on the gradual side). This assures the time difference values to have an appropriate and sufficiently large value.

In the measurement for actual subject bodies, pulse rate can vary depending on the individual difference or the health condition of the same person in the time of measurement. Accordingly, in the measurement of the oxygen saturation, the above-mentioned appropriate difference time .tm varies depending on the pulse rate of the subject person.

Figure 12C:
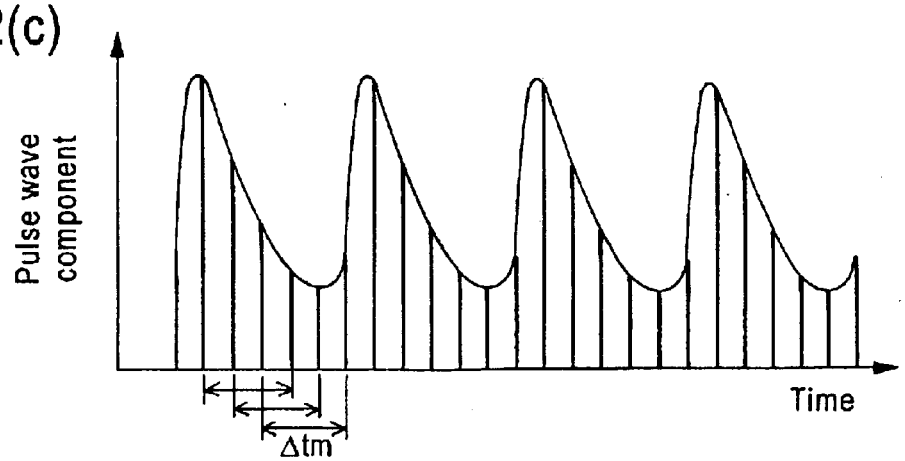

Thus, the difference time .tm is adjusted to be an appropriate value on the basis of the pulse rate information of the subject person obtained from the measurement data of the pulse wave component. More specifically, in case of a higher pulse rate as shown in FIG. 12(c), the difference time .tm is adjusted to be smaller than the difference time .tm of FIG. 12(b). Even in this case, similarly to the above-mentioned case, the difference time .tm is preferably a time interval the time difference value of which corresponds substantially to the half of the amplitude of the pulse wave waveform. Extremely large difference time .tm can result in a discrepancy in the setting value of the reference voltage between the measurement data. Accordingly, an appropriate limit value is preferably provided.

According to the above-mentioned operation of the pulse oximeter 1D, an appropriate difference time .tm is set depending on the pulse rate. This improves the S/N ratio in the time difference values, and thereby permits precise measurement of oxygen saturation.

When the difference time .tm is set appropriately depending on the pulse rate and when the difference time .tm is an integer multiple of the period corresponding to the line frequency, periodic noise of line frequency is eliminated.

Embodiment 5

The configuration of a pulse oximeter 1E according to Embodiment 5 of the invention is similar to that of the pulse oximeter 1A according to Embodiment 1. However, these pulse oximeters are different from each other in the configuration of the controller 28.

According to the configuration of the pulse oximeter 1E, dark level is measured precisely even when the dark level varies time dependently. An example of the case that the dark level varies time dependently is that the sun light is transmitted through a subject body and then detected as a dark level by the photodetector and that the intensity of the sun light varies time dependently.

In the controller 28 of the pulse oximeter 1E, a memory 28b stores a program for causing the pulse oximeter 1E to execute the operation described below.

Figure 13A:
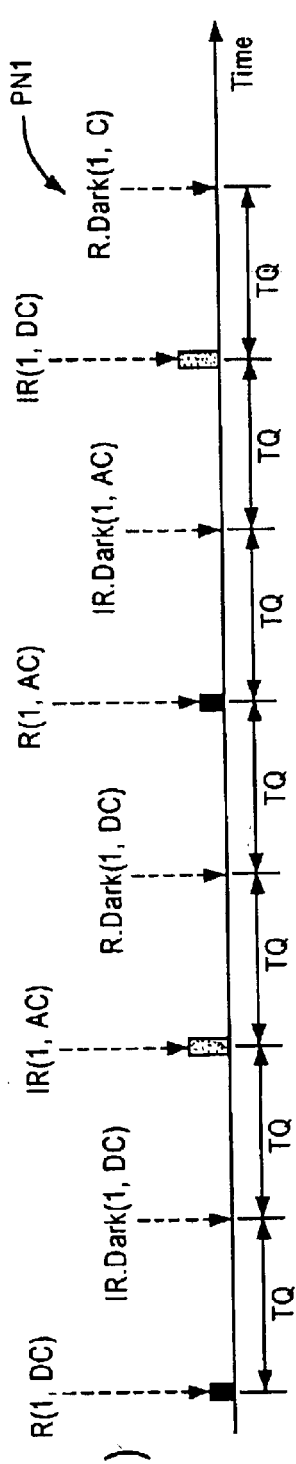
FIG. 13 illustrates the operation of a pulse oximeter 1E according to Embodiment 5 of the invention.
Figure 13B:
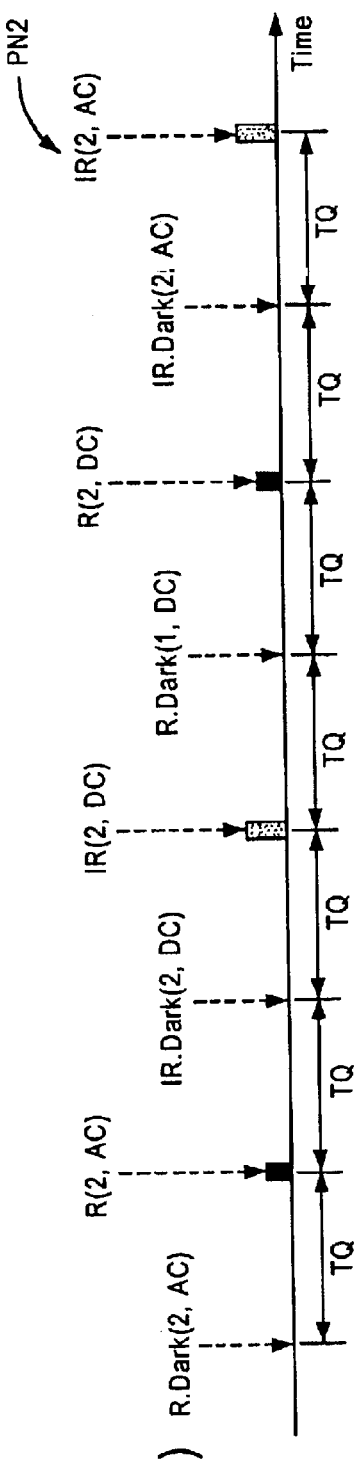
Figure 13C:
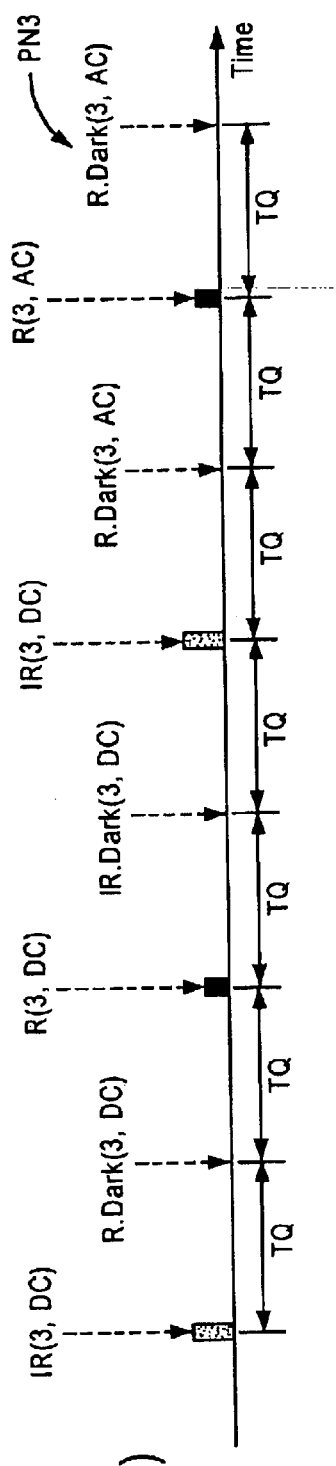

FIG. 13 illustrates the operation of a pulse oximeter 1E.

Figure 14:
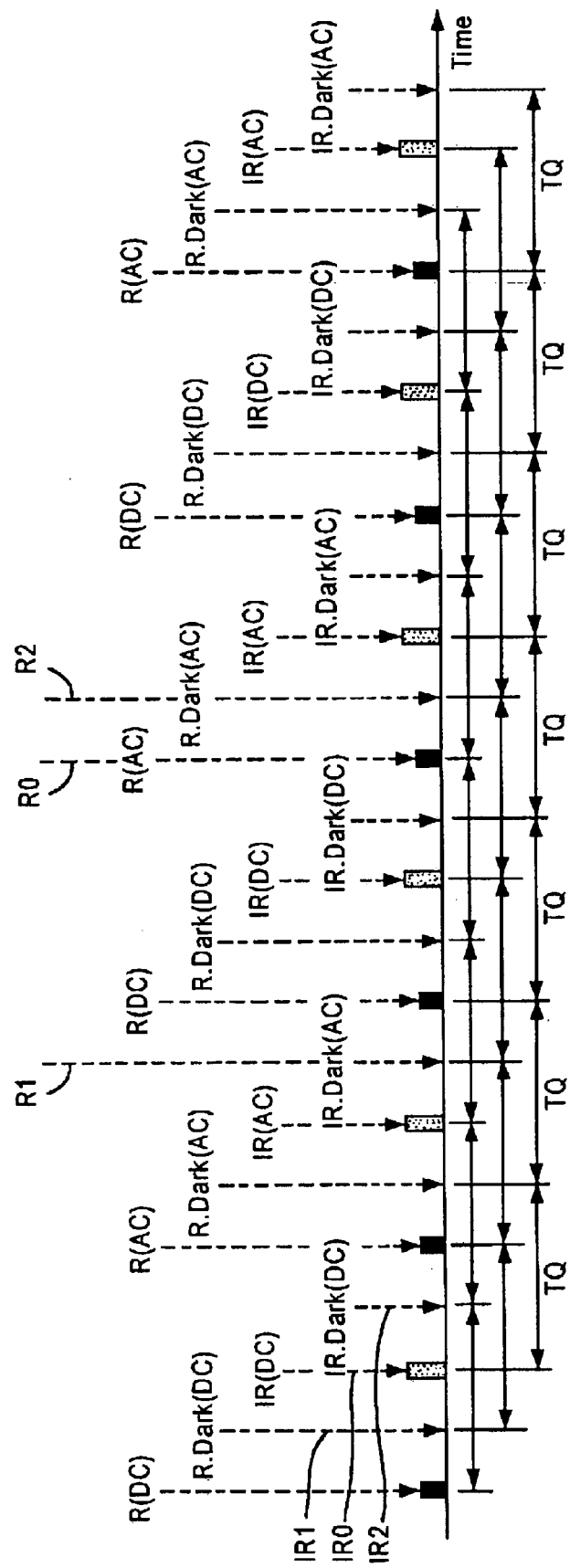
FIG. 14 illustrates the timing of measurement in a pulse oximeter 1E.

Similarly to Embodiment 3 (see FIG. 10), in the pulse oximeter 1E, used is the combination of three measurement patterns PN1-PN3 in each of which R, R.Dark, IR, and IR.Dark are measured for the transmitted light intensity DC and the pulse wave component AC. In the present embodiment, the measurement period TQ is set to be ⅛ (¹⁄₄₀₀ sec or ¹⁄₄₈₀ sec) of the period corresponding to the line frequency. FIG. 14 illustrates the overall timing of measurement composed of the three measurement patterns PN1-PN3.

The dark levels for R and IR are obtained from the interpolation of the measurement values of R.Dark and IR.Dark adjacent to the measurement timings for each of the transmitted light intensity and the pulse wave component. More specifically, the interpolation of the measurement for IR is carried out according to the following Formula (7). The interpolation of the measurement for R is carried out according to the following Formula (8).

$$Dark(t) = \frac{R.Dark\left(t - \frac{1}{3} \cdot T_Q\right) + IR.Dark\left(t + \frac{1}{3} \cdot T_Q\right)}{2} \quad (7)$$

$$Dark(t) = \frac{IR.Dark\left(t - \frac{5}{3} \cdot T_Q\right) + 5 \times R.Dark\left(t + \frac{1}{3} \cdot T_Q\right)}{6} \quad (8)$$

In order to obtain the dark level (dark level measurement value) at a timing IR0 in FIG. 14, an interpolation is carried out between the dark levels measured at timings IR1 and IR2 respectively shifted in advance and in delay by a time interval (⅓)TQ, as shown in Formula (7).

In contrast, in order to obtain the dark level (dark level measurement value) at a timing R0 in FIG. 14, an interpolation is carried out between the dark level measured at a timing R1 shifted in advance by a time interval (⁵⁄₃)TQ and the dark level measured at a timing R2 shifted in delay by a time interval (⅓)TQ, as shown in Formula (8). The difference between Formulas (7) and (8) results from that the dark level obtained during the measurement of the transmitted light intensity is used for the interpolation of the dark level for the transmitted light intensity DC, and that the dark level obtained during the measurement of the pulse wave component is used for the interpolation of the dark level for the pulse wave component AC.

As such, in the pulse oximeter 1E, a dark level corresponding to a measurement value is obtained by an interpolation between two dark levels detected at second timings closer to the measurement timing (first timing) in comparison with the above-mentioned embodiments. Then, dark level correction is carried out by subtracting this dark level from the measurement value. By virtue of this, even when the dark level varies time dependently, the influence thereof is alleviated. This permits precise measurement of oxygen saturation.

Periodic noise of the line frequency is eliminated by the calculation according to the following Formula (9). Here, N indicates an integer.

$$p = \frac{\{V_3(R) - V_3(Dark)\}_{t+8 \cdot N \cdot T_Q} - \dfrac{\{V_3(R) - V_3(Dark)\}_t}{\{V_2(R) - V_2(Dark)\}_t}}{\{V_3(IR) - V_3(Dark)\}_{t+8 \cdot N \cdot T_Q} - \dfrac{\{V_3(IR) - V_3(Dark)\}_t}{\{V_2(IR) - V_2(Dark)\}_t}} \quad (9)$$

As shown in Formula (9), in the calculation of time difference values of the pulse wave component, the difference time is set to be 8·N·TQ, whereby the p-value is calculated. In this approach, a time difference value between two measurement values (pulse wave measurement values) of the pulse wave component at measurement timings apart from each other by a time interval which is an integer multiple (N times) of the period corresponding to the line frequency is measured for each measurement pattern PN1-PN3, whereby periodic noise of the line frequency is eliminated.

The periodic noise of the line frequency has a smaller influence in the measurement of the transmitted light intensity than in the measurement of the pulse wave component. However, if necessary, smoothing operation may be carried out using a digital low-pass filter in the controller 28.

According to the operation of the pulse oximeter 1E, the dark level is interpolated between dark levels measured at timings close to the data measurement timing. Accordingly, even when the dark level varies time dependently, the blood component is measured precisely.

The present Embodiment 5 has been described for the case that the measurement period TQ is ⅛ of the period corresponding to the line frequency. However, also in the case that the measurement period is ¼, ½, 1, 2, or the like of the period corresponding to the line frequency, the difference time for the pulse wave component equals an integer multiple of the period corresponding to the line frequency. Accordingly, the same effect is obtained.

Variation in the dark level is similarly suppressed by a correction according to the following methods.

In the pulse oximeter 1B according to Embodiment 2, an interpolation is preferably carried out such as to average out the dark levels before and after a data measurement timing of R or IR as shown in FIG. 9. Also in this case, the dark level is calculated separately for the measurement of the transmitted light intensity DC and the measurement of the pulse wave component AC. The calculation is carried out according to the following Formula (10).

$$Dark = \frac{R.Dark + IR.Dark}{2} \quad (10)$$

According to this operation of Embodiment 2, variation in the dark level is suppressed, whereby the blood component is measured precisely.

In the pulse oximeter 1C according to Embodiment 3, the dark level measured separately in each phase, that is, for each measurement pattern PT1-PT3 may be extrapolated. When the variation in the dark level is obtained from another measurement pattern, the precision is improved in the calculation of the dark level.

More specifically, in order to calculate the dark level corresponding to the measurement of IR(3, AC) in the measurement pattern PT3 shown in FIG. 10(c), two dark levels in the same measurement pattern PT3 may be extrapolated according to the following Formula (11). Alternatively, dark levels measured in another phase such as the measurement pattern PT1 may be used according to the following Formula (12). In either case, variation in the dark level is suppressed, whereby the blood component is measured precisely.

$$Dark = IR.Dark(3, AC) - \frac{R.Dark(3, AC) - IR.Dark(3, AC)}{2} \quad (11)$$

$$Dark = IR.Dark(3, AC) - \frac{R.Dark(1, AC) - IR.Dark(1, AC)}{2} \quad (12)$$

Embodiment 6

The configuration of a pulse oximeter 1F according to Embodiment 6 of the invention is similar to that of the pulse oximeter 1B according to Embodiment 2. Major difference is that the reference voltage generator is removed, and that a group 29 of holding circuits described later is provided.

Figure 15:
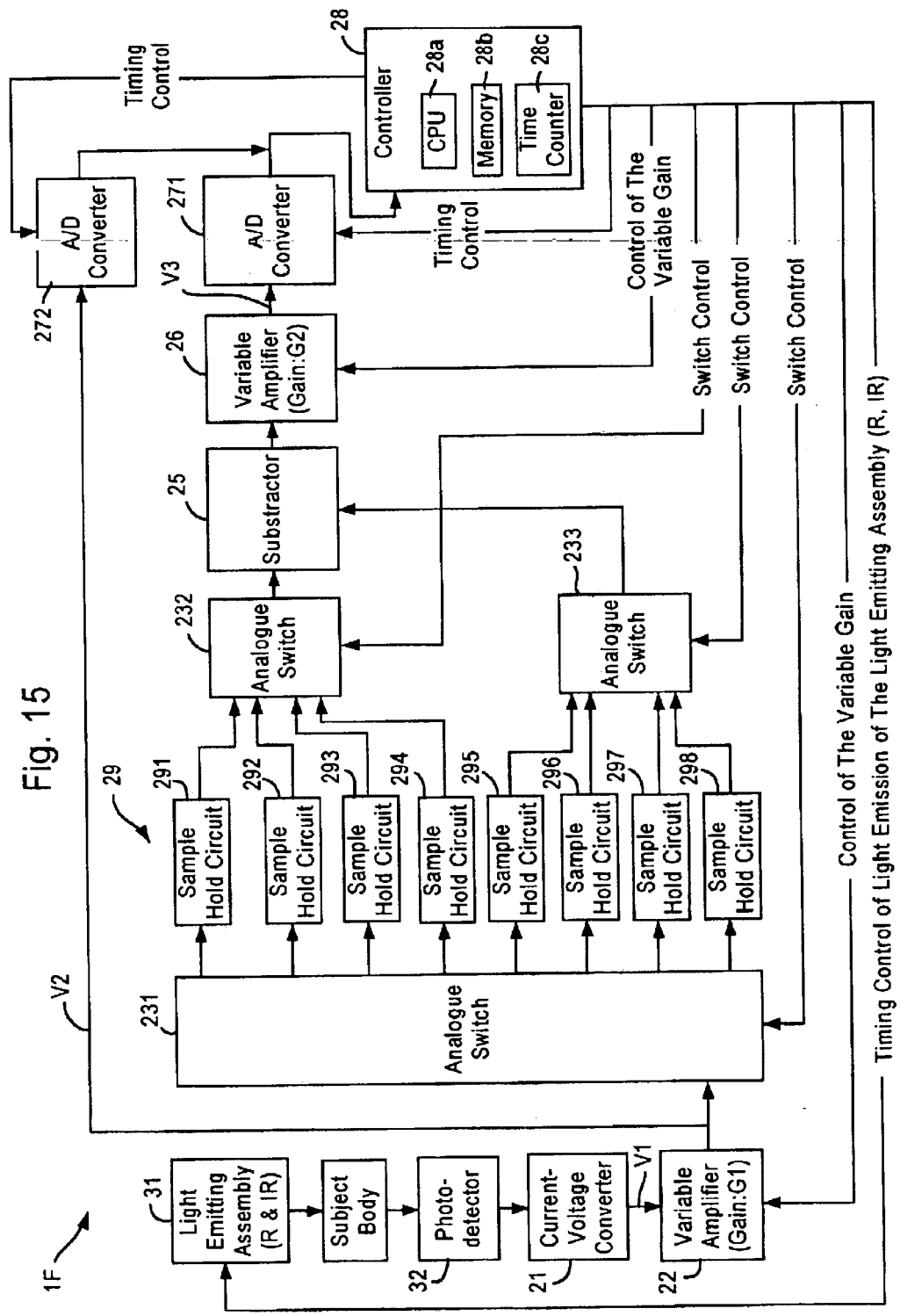
FIG. 15 shows the configuration of the measurement circuit of a pulse oximeter 1F according to Embodiment 6 of the invention.

FIG. 15 shows the configuration of the measurement circuit of the pulse oximeter 1F.

The pulse oximeter 1F comprises a voltage holding section 29 and analogue switches 232 and 233 in addition to the configuration of the pulse oximeter 1B according to Embodiment 2. The voltage holding section 29 comprises eight sample hold circuits 291–298. Each sample hold circuit 291–298 holds the input voltage thereto. The analogue switches 232 and 233 control the timing in which the measurement values held in the sample hold circuits 291–294 and 295–298, respectively, are transmitted to the controller 28.

Figure 16A:
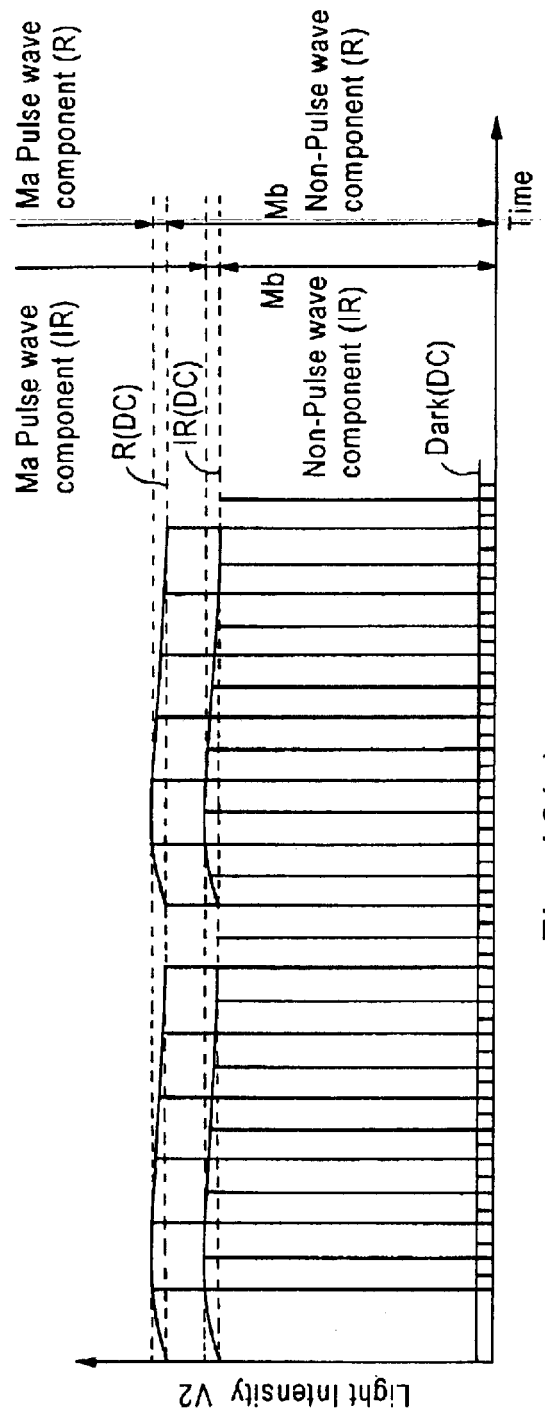
FIG. 16 illustrates the operation of a pulse oximeter 1F.
Figure 16B:
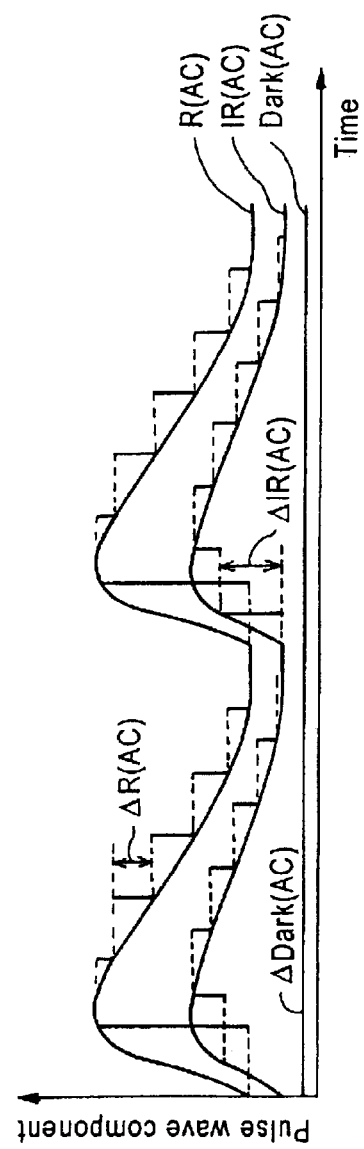

FIG. 16 illustrates the operation of the pulse oximeter 1F.

In the pulse oximeter 1F, the light emitting assembly 31 emits pulsed red light and pulsed infrared light alternately, whereby the transmitted light intensity through a subject body is measured in a time sharing manner.

Figure 17A:
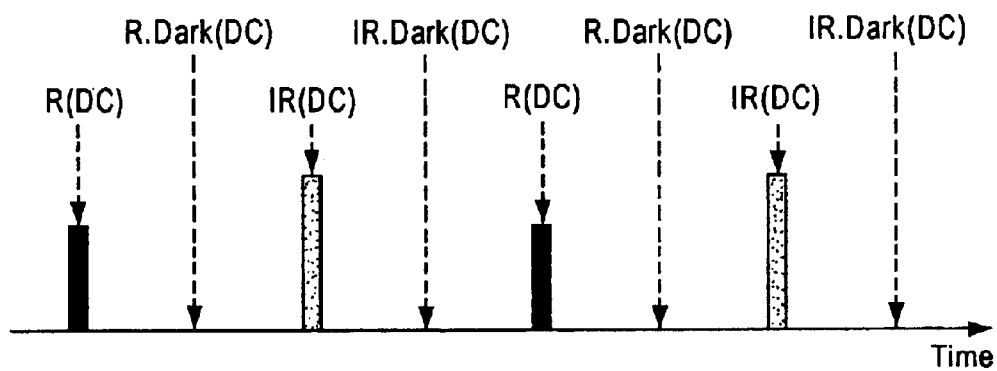
FIG. 17 illustrates the timing of measurement in a pulse oximeter 1F.

In the measurement of the transmitted light intensity DC, a signal detected by the photodetector 32 is transmitted through the current-voltage converter 21 and the variable amplifier 22, and then converted into a digital signal by the A/D converter 27. This signal is inputted to the controller 28. FIG. 17(a) illustrates the timing of measurement of the transmitted light intensity. Also in this case, measurement is carried out sequentially for R, R.Dark, IR, and IR.Dark. In order to eliminate periodic noise of the line frequency, the measurement interval is preferably set equal to an integer multiple of the period corresponding to the line frequency.

As for the measurement of the pulse wave component AC, in the above-mentioned embodiments, time difference values have been calculated by the controller 28. In contrast, in the pulse oximeter 1F according to the present embodiment, time difference values are obtained by analogue calculation in the voltage holding section 29 as follows.

Measurement values of R, R.Dark, IR, and IR.Dark are held by the two sets of sample hold circuits. Then, the voltage values V2 at measurement timings apart from each other by a difference time .t are switched alternately by the analogue switches 232 and 233, whereby time difference values of the pulse wave component are generated by the subtractor 25.

For example, in the measurement for R, the value of voltage V2 is held alternately by the sample hold circuit 291 and 295. Accordingly, the voltage value of the present measurement for R and the voltage value of the preceding measurement for R are held. The situation is the same for the other measurement (IR, R.Dark, and IR.Dark).

The voltage value held at the present measurement (for example, R) and the voltage value held at the preceding measurement (for example, R') are inputted through the analogue switches 232 and 233, respectively, to the subtractor 25 in an appropriate timing. The output from the subtractor 25 is amplified to an appropriate voltage level by the variable amplifier 26, and then converted into a digital signal by the A/D converter 271. Accordingly, a signal (for example, .R) of time difference value of the pulse wave component is inputted to the controller 28 (see FIG. 16(b)). As a result, time difference values (.R, .R.Dark, .IR, and .IR.Dark) are obtained by the analogue calculations as shown in the following Formulas (13)–(16).

$$\Delta R_{AC}(t)=V_3(R)=R_{AC}(t)-R_{AC}(t-\Delta t) \quad (13)$$

$$\Delta R.Dark_{AC}(t)=V_3(R.Dark)=R.Dark_{AC}(t)-R.Dark_{AC}(t-\Delta t) \quad (14)$$

$$\Delta IR_{AC}(t)=V_3(IR)=IR_{AC}(t)-IR_{AC}(t-\Delta t) \quad (15)$$

$$\Delta IR.Dark_{AC}(t)=V_3(IR.Dark)=IR.Dark_{AC}(t)-IR.Dark_{AC}(t-\Delta t) \quad (16)$$

Figure 17B:
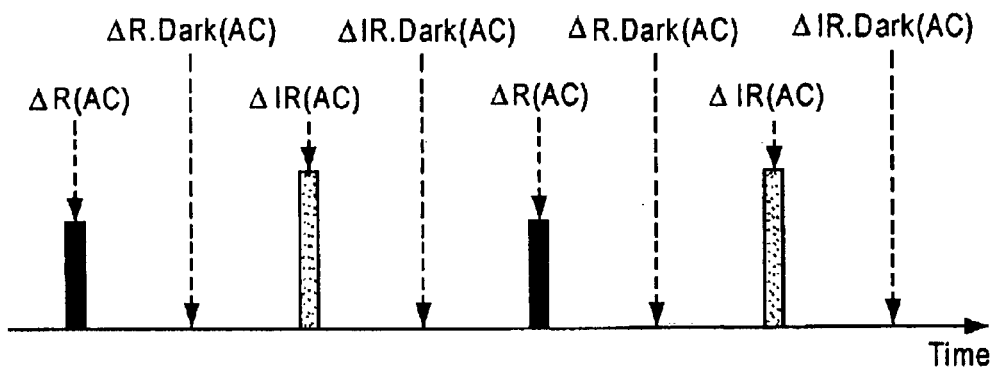

FIG. 17(b) illustrates the timing of measurement of the time difference values, while FIG. 17(a) illustrates the timing of measurement of the transmitted light intensity.

Since two sets of the sample hold circuits are switched alternately, the sign of the difference voltage outputted from the subtractor 25 is inverted also alternately into positive and negative. When the sign is inverted, the controller 28 re-inverts the sign.

Similarly to Embodiment 4, in the pulse oximeter 1F, S/N ratio in the measurement of the oxygen saturation of the blood is improved using the pulse rate information. This operation is described below.

When the p-value is calculated directly from the time difference value of the pulse wave component with respect to a small time interval as shown in FIG. 18(a), a poor S/N ratio is obtained as described above. Thus, time difference values of the pulse wave component are accumulated during a predetermined time interval .ta, for example, corresponding to 7.t as shown in FIG. 18(b). Then, the p-value is obtained according to the following Formula (17). This calculation is carried out by the controller 28.

$$p = \frac{\frac{\Sigma V_3(R) - \Sigma V_3(Dark)}{V_2(R) - V_2(Dark)}}{\frac{\Sigma V_3(IR) - \Sigma V_3(Dark)}{V_2(IR) - V_2(Dark)}} = \frac{\frac{\Sigma \Delta R(AC) - \Sigma \Delta Dark(AC)}{V_2(R) - V_2(Dark)}}{\frac{\Sigma \Delta IR(AC) - \Sigma \Delta Dark(AC)}{V_2(IR) - V_2(Dark)}} \quad (17)$$

Here, . indicates the summation of the time difference values each corresponding to a time interval .t as shown in FIG. 18(a).

Similarly to Embodiment 4, the time interval .ta shown in FIG. 18(b) is set to be a appropriate value on the basis of the pulse rate information of the subject person. More specifically, the difference time .ta is preferably a time interval the time difference value of which corresponds substantially to the half of the amplitude of the pulse wave waveform.

In the measurement of time difference values of the transmitted light intensity and the measurement of the pulse wave component, measurement operations are carried out alternately for R and IR. Accordingly, the time points of measurement are different for the measurement data of R and IR. Thus, simulated measurement values for R and IR at the same time point are calculated by interpolation of the measurement data before and after the time point of data measurement.

Similarly to Embodiment 4, according to the above-mentioned operation of the pulse oximeter 1F, an appropriate difference time is set depending on the pulse rate. This improves the S/N ratio in the time difference values, and thereby permits precise measurement of oxygen saturation. Further, time difference values are calculated in analogue circuits (the voltage holding section 29 and the like). This suppresses quantization error and the like in comparison with the case of a digital circuit (the controller 28), and thereby permits more precise measurement of the oxygen saturation.

Also in the pulse oximeter 1F, when each measurement value is sampled in a period equal to the period corresponding to the line frequency, eliminated is the influence of periodic noise of the line frequency.

In order to increase the number of measurement data points by a factor of three similarly to Embodiment 3, three times the number of sample hold circuits are necessary. This increases the number of data points, and thereby improves the precision in the measurement of oxygen saturation.

Modified Examples

Figure 20:
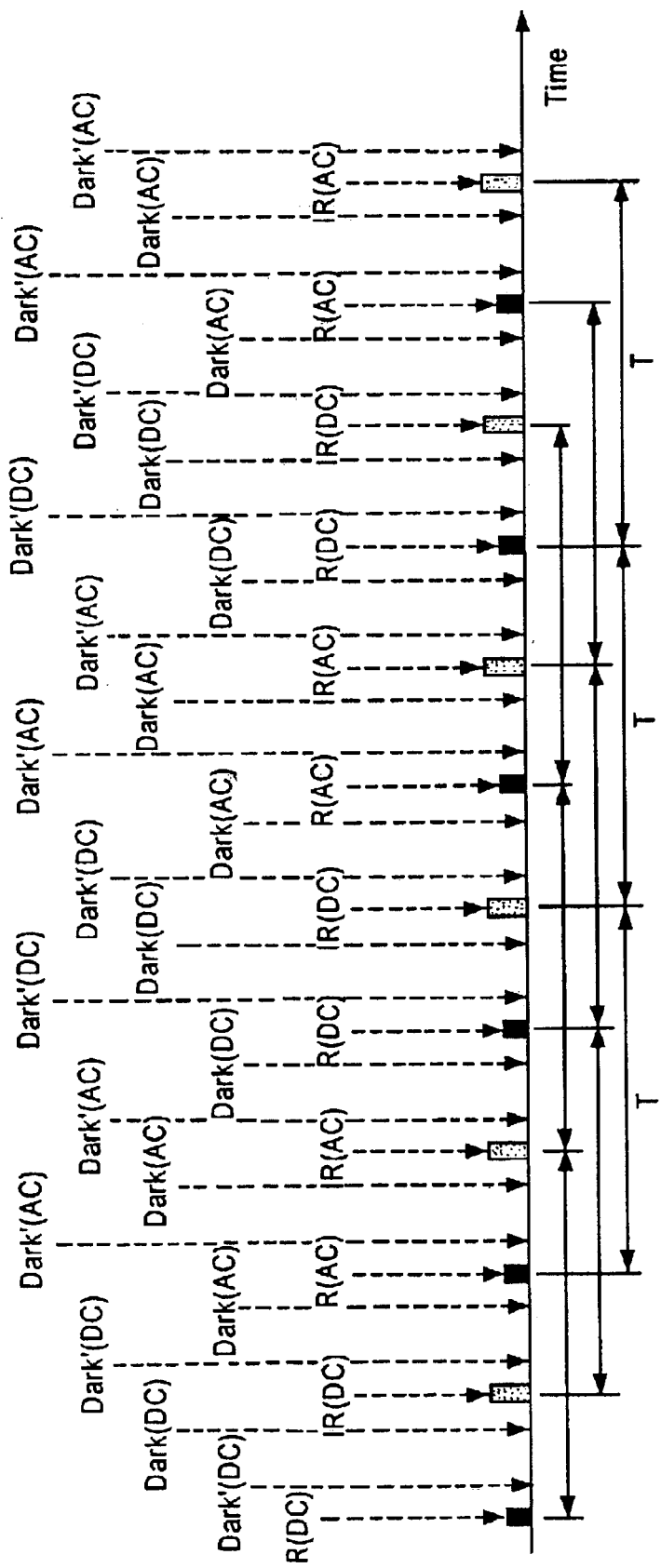
FIG. 20 illustrates the timing of measurement according to a modification of the invention.

In the above-mentioned Embodiment 3, timings of dark level measurement may be provided in the vicinity on both sides of the data measurement point of each of R and IR as shown in FIG. 19. FIG. 20 illustrates the overall timing of measurement in which three measurement patterns shown in FIGS. 19(a), 19(b), and 19(c) are superposed along the same time axis.

In the dark level correction for the data signal (R and IR) in this measurement pattern, the average of the two dark level values measured at the timings Dark and Dark' in the vicinity on both sides.

The measurement period T for each measurement pattern may be set equal to the period corresponding to the line frequency similarly to Embodiment 3, or alternatively, equal to ⅛, ¼, ½, or the like of the period corresponding to the line frequency similarly to Embodiment 5.

Also in the above-mentioned measurement patterns, when the difference time of the pulse wave component is set equal to an integer multiple of the period corresponding to the line frequency, cancelled is the noise caused by the line power and fluorescent lamps.

Also in the circuit (FIG. 8) according to Embodiment 2, the methods of measurement according to Embodiments 3 and 5 may be used.

The time intervals TO and TQ for the measurement according to Embodiments 1 and 6 are not restricted to the value equal to the period corresponding to the line frequency. The time intervals may be a value equal to an integer multiple greater than or equal to twice of the period corresponding to the line frequency. Also in this case, cancelled is the noise caused by the line power and fluorescent lamps.

Although the present invention has been fully described by way of examples with reference to the accompanying drawings, it is to be noted that various change and modifications will be apparent to those skilled in the art. Therefore, unless otherwise such changes and modifications depart from the scope of the present invention, they should be construed as being including therein.

What is claimed is:

1. A blood component measurement apparatus for measuring a blood component in the arterial blood of a subject body comprising:

an illuminating device for illuminating said subject body with predetermined light periodically at first timings;

a light intensity detector for detecting light intensity measurement values of light transmitted through said subject body;

a dark level detector for detecting dark level measurement values periodically at second timings without illumination from said illuminating device;

a pulse wave detector for extracting a pulse wave component from said light intensity measurement values, and thereby detecting pulse wave measurement values; and a blood component measurer for measuring the blood component of said arterial blood on the basis of said light intensity measurement values, said dark level measurement values, and said pulse wave measurement values;

wherein each time interval between said first timings and said second timings is an integer multiple of the period corresponding to a line frequency.

2. The blood component measurement apparatus according to claim 1, further comprising an actuator for executing a plurality of measurement operations each shifted by a predetermined phase difference of the line frequency, in the measurement in which said first timings and said second timings are repeated alternately.

3. The blood component measurement apparatus according to claim 2, further comprising a first corrector for correcting said light intensity measurement values detected at said first timings, and a second corrector for correcting said pulse wave measurement values, on the basis of said dark level measurement values detected at said second timings each shifted from each of said first timings by the integer multiple of the period corresponding to the line frequency.

4. The blood component measurement apparatus according to claim 3, further comprises a processor for applying a digital filtering process onto a time difference values of said dark-level corrected light intensity measurement values and said dark-level corrected pulse wave measurement values.

5. The blood component measurement apparatus according to claim 2, further comprising a first corrector for correcting said light intensity measurement values detected at said first timings, and a second corrector for correcting said pulse wave measurement values, on the basis of said dark level measurement values detected at said second timings each in the vicinity of each of said first timings.

6. The blood component measurement apparatus according to claim 2, wherein each of said plurality of measurement operations is the combination of: the measurement of light intensity measurement values; the measurement of dark level measurement values used for the correction of said light intensity measurement values; the measurement of pulse wave measurement values; and the measurement of dark level measurement values used for the correction of said pulse wave measurement values.

7. The blood component measurement apparatus according to claim 2, wherein said predetermined phase difference in said plurality of measurement operations is a time difference generated by dividing an integer multiple of the period corresponding to the line frequency by the number of said plurality of measurement operations.

8. The blood component measurement apparatus according to claim 1, further comprising a calculator for calculating a time difference value of two pulse wave measurement values detected with a time interval equal to the integer multiple of the period corresponding to the line frequency, wherein said blood component measurer measures said blood component also on the basis of said time difference value.

9. The blood component measurement apparatus according to claim 1, wherein said illuminating device illuminates said subject body alternately with two kinds of light having wavelengths different from each other.

10. The blood component measurement apparatus according to claim 9, wherein said illuminating device illuminates a red light and an infrared light.

11. The blood component measurement apparatus according to claim 9, further comprising: a first generator for correcting said light intensity measurement values on the basis of said dark level measurement values, and thereby generating corrected light intensity measurement values;

a second generator for correcting said pulse wave measurement values on the basis of said dark level measurement values, and thereby generating corrected pulse wave measurement values;

an interpolator for interpolating one of said corrected light intensity measurement values and one of said corrected pulse wave measurement values detected by illuminating with said two kinds of light having different wavelengths at timings different from each other, using said corrected measurement values before and after the timing of illumination; and a calculator for calculating a simulated value of said corrected light intensity measurement value and a simulated value of said corrected pulse wave measurement value which are simulated as if measured at the same timing when said two kinds of light having different wavelengths illuminate simultaneously, on the basis of the interpolation carried out in said interpolator.

12. The blood component measurement apparatus according to claim 9, wherein said light intensity detector detects said light intensity measurement values amplified by using a first gain, and when said illuminating device does not illuminate said subject body, said dark level detector detects said dark level measurement values amplified by using a second gain equal to said first gain.

13. The blood component measurement apparatus according to claim 9, wherein said pulse wave detector detects said pulse wave measurement values amplified by using a first gain, and when said illuminating device does not illuminate said subject body, said dark level detector detects said dark level measurement values amplified by using a second gain equal to said first gain.

14. A method of measuring a blood component in the arterial blood of a subject body, comprising the steps of:

illuminating said subject body with predetermined light periodically at first timings by an illuminating device;

detecting light intensity measurement values of light transmitted through said subject body;

extracting a pulse wave component from said light intensity measurement values, and thereby detecting pulse wave measurement values;

detecting dark level measurement values periodically at second timings without illumination from said illuminating device; and measuring the blood component of said arterial blood on the basis of said light intensity measurement values, said dark level measurement values, and said pulse wave measurement values;

wherein each time interval between said first timings and said second timings is an integer multiple of the period corresponding to a line frequency.

* * * * *